US012788566B2

(12) United States Patent
Gilson et al.

(10) Patent No.: US 12,788,566 B2
(45) Date of Patent: Nov. 10, 2026

(54) KNEE CONE AUGMENTS AND ASSOCIATED SURGICAL BROACHES FOR USE IN AN ORTHOPAEDIC SURGICAL PROCEDURE

(71) Applicant: DEPUY IRELAND UNLIMITED COMPANY, Ringaskiddy (IE)

(72) Inventors: Lindsay L. Gilson, Columbia City, IN (US); Anthony J. Webb, Fort Wayne, IN (US); Jeremiah M. Lewis, Warsaw, IN (US); Matthew D. Schmit, Columbia City, IN (US); Wesley J. Gardner, Warsaw, IN (US); Stephanie Recker, Warsaw, IN (US); Elizabeth Wiederhold, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1322 days.

(21) Appl. No.: 17/557,635

(22) Filed: Dec. 21, 2021

(65) Prior Publication Data

US 2023/0190477 A1 Jun. 22, 2023

(51) Int. Cl.
*A61F 2/30* (2006.01)
*A61B 17/16* (2006.01)
(Continued)

(52) U.S. Cl.
CPC ...... *A61F 2/30734* (2013.01); *A61B 17/1675* (2013.01); *A61F 2/3859* (2013.01);
(Continued)

(58) Field of Classification Search
CPC .... A61F 2/30734; A61F 2/3859; A61F 2/389; A61F 2/461; A61F 2/4684; A61F 2002/30215; A61F 2002/30326; A61F 2002/30736; A61B 17/1675; A61B 17/1617; A61B 17/164; A61B 17/1659
See application file for complete search history.

(56) References Cited

U.S. PATENT DOCUMENTS

| | | | |
|---|---|---|---|
| 2,947,308 | A | 8/1960 | Gorman |
| D230,429 | S | 2/1974 | Davidson et al. |

(Continued)

FOREIGN PATENT DOCUMENTS

| | | |
|---|---|---|
| DE | 7716147 U1 | 10/1977 |
| EP | 532585 B1 | 4/2000 |

(Continued)

OTHER PUBLICATIONS

PCT International Search Report for International Application No. PCT/EP2022/087016; Mar. 16, 2023; 24 pages.

(Continued)

*Primary Examiner* — Melanie R Tyson
*Assistant Examiner* — Rachel S Highland
(74) *Attorney, Agent, or Firm* — Barnes & Thornburg LLP

(57) ABSTRACT

An orthopaedic joint replacement system is shown and described. The system includes a number of prosthetic components configured to be implanted into a patient's knee. The system also includes a number of surgical instruments configured for use in preparing the bones of the patient's knee to receive the implants. A number of methods for using the surgical instruments to prepare the bones is also disclosed.

15 Claims, 28 Drawing Sheets

(51) Int. Cl.
*A61F 2/38* (2006.01)
*A61F 2/46* (2006.01)

(52) U.S. Cl.
CPC .............. *A61F 2/389* (2013.01); *A61F 2/461* (2013.01); *A61F 2/4684* (2013.01); *A61F 2002/30215* (2013.01); *A61F 2002/30326* (2013.01); *A61F 2002/30736* (2013.01)

(56) References Cited

U.S. PATENT DOCUMENTS

| | | | |
|---|---|---|---|
| 3,891,997 | A | 7/1975 | Herbert |
| 4,136,405 | A | 1/1979 | Pastrick et al. |
| 4,164,794 | A | 8/1979 | Spector et al. |
| 4,206,516 | A | 6/1980 | Pilliar |
| 4,216,549 | A | 8/1980 | Hillberry et al. |
| 4,219,893 | A | 9/1980 | Noiles |
| 4,224,696 | A | 9/1980 | Murray et al. |
| 4,523,587 | A | 6/1985 | Frey |
| 4,659,331 | A | 4/1987 | Matthews et al. |
| 4,711,639 | A | 12/1987 | Grundei |
| 4,790,852 | A | 12/1988 | Noiles |
| 4,822,366 | A | 4/1989 | Bolesky |
| 4,827,919 | A | 5/1989 | Barbarito et al. |
| 4,883,488 | A | 11/1989 | Bloebaum et al. |
| 4,888,021 | A | 12/1989 | Forte et al. |
| 4,944,757 | A | 7/1990 | Martinez et al. |
| 4,950,298 | A | 8/1990 | Gustilo et al. |
| 5,019,103 | A | 5/1991 | Van Zile et al. |
| 5,059,196 | A | 10/1991 | Coates |
| 5,152,797 | A | 10/1992 | Luckman et al. |
| 5,197,488 | A | 3/1993 | Kovacevic |
| 5,226,915 | A | 7/1993 | Bertin |
| 5,246,459 | A | 9/1993 | Elias |
| 5,356,414 | A | 10/1994 | Cohen et al. |
| 5,358,527 | A | 10/1994 | Forte |
| 5,358,530 | A | 10/1994 | Hodorek |
| 5,370,693 | A | 12/1994 | Kelman et al. |
| 5,387,241 | A | 2/1995 | Hayes |
| 5,413,604 | A | 5/1995 | Hodge |
| 5,480,445 | A | 1/1996 | Burkinshaw |
| 5,489,311 | A | 2/1996 | Cipolletti |
| 5,549,685 | A | 8/1996 | Hayes |
| 5,609,645 | A | 3/1997 | Vinciguerra |
| 5,658,349 | A | 8/1997 | Brooks et al. |
| 5,766,256 | A | 6/1998 | Oudard et al. |
| 5,782,925 | A | 7/1998 | Collazo et al. |
| 5,824,103 | A | 10/1998 | Williams |
| 5,951,564 | A | 9/1999 | Schroder et al. |
| 5,957,979 | A | 9/1999 | Beckman et al. |
| 5,984,968 | A | 11/1999 | Park |
| 5,997,581 | A | 12/1999 | Khalili |
| 6,039,764 | A | 3/2000 | Pottenger et al. |
| 6,071,311 | A | 6/2000 | O'Neil et al. |
| 6,074,424 | A | 6/2000 | Perrone, Jr. et al. |
| 6,080,195 | A | 6/2000 | Colleran et al. |
| 6,117,175 | A | 9/2000 | Bosredon |
| 6,126,691 | A | 10/2000 | Kasra et al. |
| 6,139,581 | A | 10/2000 | Engh et al. |
| 6,139,584 | A | 10/2000 | Ochoa et al. |
| 6,152,963 | A | 11/2000 | Noiles et al. |
| 6,162,254 | A | 12/2000 | Timoteo |
| 6,171,342 | B1 | 1/2001 | O'Neil et al. |
| 6,264,699 | B1 | 7/2001 | Noiles et al. |
| 6,423,096 | B1 | 7/2002 | Musset et al. |
| 6,428,578 | B2 | 8/2002 | White |
| 6,447,549 | B1 | 9/2002 | Taft |
| 6,613,092 | B1 | 9/2003 | Kana et al. |
| 7,105,026 | B2 | 9/2006 | Johnson et al. |
| 7,208,222 | B2 | 4/2007 | Rolfe et al. |
| 7,291,174 | B2 | 11/2007 | German et al. |
| 7,846,212 | B2 | 12/2010 | Lewis et al. |
| 7,892,288 | B2 | 2/2011 | Blaylock et al. |
| 8,382,849 | B2 | 2/2013 | Thomas |
| 8,721,733 | B2 | 5/2014 | Bonitati |
| 8,900,317 | B2 | 12/2014 | Zubok et al. |
| 8,998,996 | B2 | 4/2015 | James et al. |
| 9,011,444 | B2 | 4/2015 | Primiano et al. |
| 9,149,282 | B2 | 10/2015 | Servidio et al. |
| 9,526,513 | B2 | 12/2016 | Collazo et al. |
| 9,554,810 | B2 * | 1/2017 | Tsukayama ........ A61B 17/1659 |
| 9,668,758 | B2 | 6/2017 | Collazo et al. |
| 10,085,841 | B2 | 10/2018 | Blaylock et al. |
| 10,524,806 | B2 | 1/2020 | Collazo et al. |
| 10,893,947 | B2 | 1/2021 | Blaylock et al. |
| 2002/0072802 | A1 | 6/2002 | O'Neil et al. |
| 2003/0171815 | A1 | 9/2003 | Kana et al. |
| 2004/0049270 | A1 | 3/2004 | Gewirtz |
| 2004/0049284 | A1 | 3/2004 | German et al. |
| 2004/0117024 | A1 | 6/2004 | Gerbec et al. |
| 2004/0162619 | A1 | 8/2004 | Blaylock et al. |
| 2005/0107883 | A1 | 5/2005 | Goodfried et al. |
| 2007/0088443 | A1 | 4/2007 | Hanssen et al. |
| 2008/0167722 | A1 | 7/2008 | Metzger et al. |
| 2008/0281430 | A1 | 11/2008 | Kelman et al. |
| 2010/0114323 | A1 | 5/2010 | Deruntz et al. |
| 2013/0178947 | A1 | 7/2013 | Monaghan et al. |
| 2014/0081411 | A1 * | 3/2014 | Lieberman .............. A61F 2/389 623/20.15 |
| 2014/0257293 | A1 | 9/2014 | Axelson, Jr. et al. |
| 2014/0277528 | A1 | 9/2014 | Mines et al. |
| 2018/0008416 | A1 | 1/2018 | Vergari et al. |

FOREIGN PATENT DOCUMENTS

| | | | |
|---|---|---|---|
| EP | 863731 | B1 | 4/2001 |
| EP | 2540255 | A1 | 1/2013 |
| EP | 2668932 | A1 | 12/2013 |
| JP | 10277069 | A | 10/1998 |
| JP | 2001526573 | A | 12/2001 |
| WO | 9118563 | A1 | 12/1991 |
| WO | 9718776 | A1 | 5/1997 |
| WO | 9730661 | A1 | 8/1997 |
| WO | 9852499 | A1 | 11/1998 |
| WO | 9932053 | A1 | 7/1999 |
| WO | 0205732 | A1 | 1/2002 |
| WO | 2009089581 | A1 | 7/2009 |
| WO | 2015145348 | A1 | 10/2015 |

OTHER PUBLICATIONS

Exactech Knee Operative Technique Addendum, OPTETRAK LOGIC® Metaphyseal Cones, 2016, 20 pages.

Zimmer Biomet, Persona Revision Knee System, Surgical Technique, 2019, 72 pages.

Zimmer Biomet, Persona Revision Knee System, Large Defect Surgical Technique, 2019, 14 pages.

Zimmer Biomet, Trabecular Metal Tibial and Femoral Cones, Surgical Technique, 2020, 64 pages.

Stryker, Triathlon Revision Knee System, Surgical Protocol, 2016, 92 pages.

* cited by examiner

KNEE CONE AUGMENTS AND ASSOCIATED SURGICAL BROACHES FOR USE IN AN ORTHOPAEDIC SURGICAL PROCEDURE

CROSS-REFERENCE TO RELATED APPLICATIONS

Cross reference is made to U.S. patent application Ser. No. 17/557,629, now U.S. Pat. No. 12,115,084, entitled "METHOD OF INSTALLING A KNEE CONE AUGMENT IN AN ORTHOPAEDIC SURGICAL PROCEDURE;" and U.S. patent application Ser. No. 17/557,620 entitled "MODULAR TIBIAL CONE AUGMENTS AND METHOD OF SURGICALLY USING THE SAME;" each of which is assigned to the same assignee as the present application, each of which is filed concurrently herewith, and each of which is hereby incorporated by reference.

TECHNICAL FIELD

The present disclosure relates generally to an orthopaedic system, including prosthetic components, surgical instruments, and methods for use in the performance of an orthopaedic joint replacement procedure, and more particularly to orthopaedic prosthetic components, surgical instruments, and methods for use in the performance of a knee replacement procedure.

BACKGROUND

Joint arthroplasty is a well-known surgical procedure by which a diseased and/or damaged natural joint is replaced by a prosthetic joint. For example, in a knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared intramedullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, commonly referred to a "primary knee prosthesis," is surgically removed and a replacement or "revision knee prosthesis" is implanted. In some revision knee surgeries, all of the components of the primary knee prosthesis, including, for example, the tibial tray, the femoral component, and the polymer bearing, may be surgically removed and replaced with revision prosthetic components.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial component that may be used to size and select a prosthetic stem component.

Moreover, during a revision knee surgery, the orthopaedic surgeon may use an augment in combination with the revision tibial tray and/or the revision femoral component to compensate for bone loss associated with removal of the primary knee prosthesis or other defects in the patient's tibia and/or femur. There are two types of commonly used knee augments—sleeve augments and cone augments. A sleeve augment is mechanically locked to one or more of the components of the revision knee prosthesis prior to implantation of the prosthesis into the patient's bone. For example, a tibial sleeve augment is mechanically locked (e.g., via a taper lock or fastener) to the tibial stem component and/or the tibial tray prior to implantation of the tibial revision prosthesis into the tibia of the patient, whereas a femoral sleeve augment is mechanically locked (e.g., via a taper lock or fastener) to the femoral stem component and/or the femoral component prior to implantation of the femoral revision prosthesis into the femoral of the patient. Cone augments, on the other hand, are not directly locked to the revision knee prosthesis prior to implantation of the prosthesis in the bone of the patient. Instead, a cone augment is first separately implanted into the bone of the patient. Thereafter, the revision knee prosthesis is then implanted into the bone of the patient through the implanted cone augment. Then, the implanted revision knee prosthesis may be secured to the previously-implanted cone augment by use of, for example, bone cement. In the case of a press-fit "cementless" revision knee prosthesis, the implanted prosthesis is not cemented or otherwise secured to the previously-implanted cone augment. For example, a tibial cone augment is first separately implanted in the tibia of a patient, with a tibial revision prosthesis then being implanted such that its tibial stem component extends through the tibial cone augment. Subsequent to implantation of the tibial revision prosthesis, bone cement may be used to secure the tibial stem component and the tibial tray to the tibial cone augment (although use of bone cement may be omitted in the case of use of a cementless tibial revision prosthesis). Similarly, in the case of a femoral procedure, a femoral cone augment is first separately implanted in the femur of a patient, with a femoral revision prosthesis then being implanted such that its femoral stem component extends through the femoral cone augment. Subsequent to implantation of the femoral revision prosthesis, bone cement may be used to secure the femoral stem component and the femoral component to the femoral cone augment (although use of bone cement may be omitted in the case of use of a cementless femoral revision prosthesis).

SUMMARY

An orthopaedic joint replacement system is shown and described. The system includes a number of prosthetic components configured to be implanted into a patient's knee. The system also includes a number of surgical instruments configured for use in preparing the bones of the patient's knee to receive the implants. Methods or techniques for using the surgical instruments to prepare the patient's bones are also disclosed.

According to one aspect of the disclosure, a method of surgically preparing a proximal end of a tibia of a patient includes reaming an intramedullary canal of the tibia with a canal reamer. The method also includes attaching a proximal end of a stem trial component to a distal end of a surgical broach, and thereafter advancing a distal end of the stem trial component within the reamed intramedullary canal of the tibia. The method also includes broaching the proximal end of the tibia using the surgical broach secured to the stem trial component during advancement of the distal end of the stem trial component within the reamed intramedullary canal of the tibia so as to form a surgically-prepared broached cavity in the proximal end of the tibia. A tibial cone augment is then installed in the broached cavity formed in the proximal end of the tibia.

In an embodiment, the proximal end of the tibia may be reamed using a cone reamer secured to the stem trial component so as to form a surgically-prepared reamed cavity in the proximal end of the tibia prior to broaching the proximal end of the tibia. In such an embodiment, the surgical broach is advanced into the reamed cavity formed in the proximal end of the tibia during advancement of the distal end of the stem trial component within the reamed intramedullary canal of the tibia so as to form the surgically-prepared broached cavity in the proximal end of the tibia.

In an embodiment, the stem trial component guides advancement of the surgical broach during broaching of the proximal end of the tibia.

The canal reamer is removed from the intramedullary canal prior to advancement of the distal end of the stem trial component within the reamed intramedullary canal.

The method also includes removing a previously-installed tibial implant from the tibia of the patient prior to reaming the intramedullary canal of the tibia with the canal reamer.

According to another aspect of the disclosure, a method of surgically preparing a distal end of a femur of a patient includes reaming an intramedullary canal of the femur with a canal reamer. The method also includes attaching a proximal end of a stem trial component to a distal end of a surgical broach, and thereafter advancing a distal end of the stem trial component within the reamed intramedullary canal of the femur. The method also includes broaching the distal end of the femur using the surgical broach secured to the stem trial component during advancement of the distal end of the stem trial component within the reamed intramedullary canal of the femur so as to form a surgically-prepared broached cavity in the distal end of the femur. A femoral cone augment is then installed in the broached cavity formed in the distal end of the femur.

In an embodiment, the distal end of the femur may be reamed using a cone reamer secured to the stem trial component so as to form a surgically-prepared reamed cavity in the distal end of the femur prior to broaching the distal end of the femur. In such an embodiment, the surgical broach is advanced into the reamed cavity formed in the distal end of the femur during advancement of the distal end of the stem trial component within the reamed intramedullary canal of the femur so as to form the surgically-prepared broached cavity in the distal end of the femur.

In an embodiment, the stem trial component guides advancement of the surgical broach during broaching of the distal end of the femur.

The canal reamer is removed from the intramedullary canal prior to advancement of the distal end of the stem trial component within the reamed intramedullary canal.

The method also includes removing a previously-installed femoral implant from the femur of the patient prior to reaming the intramedullary canal of the femur with the canal reamer.

According to yet another aspect of the disclosure, a method of surgically preparing a knee of a patient includes reaming an intramedullary canal of a tibia of the patient with a tibial canal reamer, and thereafter broaching a proximal end of the tibia using a surgical broach secured to a stem trial component positioned in the reamed intramedullary canal of the tibia so as to form a surgically-prepared broached cavity in the proximal end of the tibia. A tibial cone augment is then installed in the broached cavity formed in the proximal end of the tibia.

In an embodiment, the proximal end of the tibia is reamed using a cone reamer secured to the stem trial component positioned in the reamed intramedullary canal of the tibia so as to form a surgically-prepared reamed cavity in the proximal end of the tibia prior to broaching the proximal end of the tibia. In such an embodiment, the surgical broach is advanced into the reamed cavity formed in the proximal end of the tibia.

In an embodiment, the stem trial component guides advancement of the surgical broach during broaching of the proximal end of the tibia.

The canal reamer is removed from the intramedullary canal prior to advancement of the distal end of the stem trial component within the reamed intramedullary canal.

The method also includes removing a previously-installed tibial implant from the tibia of the patient prior to reaming the intramedullary canal of the tibia with the canal reamer.

According to a further aspect of the disclosure, a method of surgically preparing a knee of a patient includes reaming an intramedullary canal of a femur of the patient with a femoral canal reamer, and thereafter broaching a distal end of the femur using a surgical broach secured to a stem trial component positioned in the reamed intramedullary canal of the femur so as to form a surgically-prepared broached cavity in the distal end of the femur. A femoral cone augment is then installed in the broached cavity formed in the distal end of the femur.

In an embodiment, the distal end of the femur is reamed using a cone reamer secured to the stem trial component positioned in the reamed intramedullary canal of the femur so as to form a surgically-prepared reamed cavity in the distal end of the femur prior to broaching the distal end of the femur. In such an embodiment, the surgical broach is advanced into the reamed cavity formed in the distal end of the femur.

In an embodiment, the stem trial component guides advancement of the surgical broach during broaching of the distal end of the femur.

The canal reamer is removed from the intramedullary canal prior to advancement of the distal end of the stem trial component within the reamed intramedullary canal.

The method also includes removing a previously-installed femoral implant from the femur of the patient prior to reaming the intramedullary canal of the femur with the canal reamer.

According to another aspect of the disclosure, an orthopaedic system includes a plurality of tibial cone augments configured to be implanted into a surgically-prepared cavity in a proximal end of a tibia of a patient. Each of the plurality of tibial cone augments has (i) a medial/lateral augment taper angle that is the same as each of the other of the plurality of tibial cone augments, and (ii) a medial/lateral augment width that is different from each of the other of the plurality of tibial cone augments. The orthopaedic system also includes a plurality of tibial surgical broaches having cutting teeth configured to cut and remove bone to form the surgically-prepared cavity in the proximal end of the tibia of the patient. Each of the plurality of tibial surgical broaches has (i) a medial/lateral broach taper angle that is the same as each of the other of the plurality of tibial surgical broaches, the medial/lateral broach taper angle being the same as the medial/lateral augment taper angle, and (ii) a medial/lateral broach width that is different from each of the other of the plurality of tibial surgical broaches.

In an embodiment, each of the plurality of tibial cone augments has an anterior/posterior augment taper angle that is the same as each of the other of the plurality of tibial cone augments, and each of the plurality of tibial surgical broaches has an anterior/posterior broach taper angle that is the same as each of the other of the plurality of tibial surgical broaches, with the anterior/posterior broach taper angle being the same as the anterior/posterior augment taper angle.

In an illustrative embodiment, each of the plurality of tibial cone augments is embodied as a tri-lobe tibial cone augment. In another embodiment, each of the plurality of tibial cone augments is embodied as a bi-lobe tibial cone augment.

The orthopaedic system may also include a stem trial component having a threaded post extending from a proximal end thereof. In such an embodiment, each of the plurality of tibial surgical broaches has a threaded aperture formed in a distal end thereof that is sized to threadingly receive the threaded post of the stem trial component.

According to a further aspect, an orthopaedic system includes a plurality of femoral cone augments configured to be implanted into a surgically-prepared cavity in a distal end of a femur of a patient. Each of the plurality of femoral cone augments has (i) a medial/lateral augment taper angle that is the same as each of the other of the plurality of femoral cone augments, and (ii) a medial/lateral augment width that is different from each of the other of the plurality of femoral cone augments. The orthopaedic system also includes a plurality of femoral surgical broaches having cutting teeth configured to cut and remove bone to form the surgically-prepared cavity in the distal end of the femur of the patient. Each of the plurality of femoral surgical broaches has (i) a medial/lateral broach taper angle that is the same as each of the other of the plurality of femoral surgical broaches, the medial/lateral broach taper angle being the same as the medial/lateral augment taper angle, and (ii) a medial/lateral broach width that is different from each of the other of the plurality of femoral surgical broaches.

In an embodiment, each of the plurality of femoral cone augments has an anterior/posterior augment taper angle that is the same as each of the other of the plurality of femoral cone augments, and each of the plurality of femoral surgical broaches has an anterior/posterior broach taper angle that is the same as each of the other of the plurality of femoral surgical broaches, with the anterior/posterior broach taper angle being the same as the anterior/posterior augment taper angle.

The orthopaedic system may also include a stem trial component having a threaded post extending from a proximal end thereof. In such an embodiment, each of the plurality of femoral surgical broaches has a threaded aperture formed in a distal end thereof that is sized to threadingly receive the threaded post of the stem trial component.

According to yet another aspect of the disclosure, an orthopaedic system includes a plurality of knee cone augments configured to be implanted into a surgically-prepared cavity in an end of a bone of a patient's knee. Each of the plurality of knee cone augments has (i) a medial/lateral augment taper angle that is the same as each of the other of the plurality of knee cone augments, and (ii) a medial/lateral augment width that is different from each of the other of the plurality of knee cone augments. The orthopaedic system also includes a plurality of knee surgical broaches having cutting teeth configured to cut and remove bone to form the surgically-prepared cavity in the end of the bone of the patient's knee. Each of the plurality of knee surgical broaches has (i) a medial/lateral broach taper angle that is the same as each of the other of the plurality of knee surgical broaches, the medial/lateral broach taper angle being the same as the medial/lateral augment taper angle, and (ii) a medial/lateral broach width that is different from each of the other of the plurality of knee surgical broaches.

In an embodiment, each of the plurality of knee cone augments has an anterior/posterior augment taper angle that is the same as each of the other of the plurality of knee cone augments, and each of the plurality of knee surgical broaches has an anterior/posterior broach taper angle that is the same as each of the other of the plurality of knee surgical broaches, with the anterior/posterior broach taper angle being the same as the anterior/posterior augment taper angle.

In an illustrative embodiment, each of the plurality of knee cone augments is embodied as a tri-lobe tibial cone augment. In another embodiment, each of the plurality of knee cone augments is embodied as a bi-lobe tibial cone augment. In yet another illustrative embodiment, each of the plurality of knee cone augments is embodied as a femoral cone augment.

The orthopaedic system may also include a stem trial component having a threaded post extending from a proximal end thereof. In such an embodiment, each of the plurality of knee surgical broaches has a threaded aperture formed in a distal end thereof that is sized to threadingly receive the threaded post of the stem trial component.

According to a further aspect of the disclosure, a method of surgically preparing an end of a bone of a patient's knee includes selecting a knee surgical broach having cutting teeth configured to cut bone from a plurality of knee surgical broaches, wherein the selected knee surgical broach has a medial/lateral broach taper angle that is the same as each of the other of the plurality of knee surgical broaches. The selected broach is then advanced into the end of the bone of the patient's knee so as to form a surgically-prepared cavity therein. A knee cone augment is then selected from a plurality of knee cone augments. The selected knee cone augment has (i) a medial/lateral augment taper angle that is the same as the medial/lateral broach taper angle, and (ii) a medial/lateral augment width that is smaller than a medial/lateral broach width of the selected knee surgical broach. Thereafter, the selected knee cone augment is implanted into the surgically-prepared cavity formed in the end of the bone of the patient's knee.

In one embodiment, the selected knee cone augment is a tibial cone augment that is implanted in a proximal end of a tibia of the patient's knee. In another embodiment, the selected knee cone augment is a tri-lobe tibial cone augment that is implanted in a proximal end of a tibia of the patient's knee. In yet another embodiment, the selected knee cone augment is a bi-lobe tibial cone augment that is implanted in a proximal end of a tibia of the patient's knee. In a further embodiment, the selected knee cone augment is a femoral cone augment that is implanted in a distal end of a femur of the patient's knee.

According to another aspect of the disclosure, an orthopaedic knee implant includes a modular tibial cone augment configured to be implanted into a surgically-prepared cavity in a proximal end of a tibia of a patient. The modular tibial cone augment includes a central lobe component having: (i) a round elongated body, (ii) a bore configured to receive a stem of a revision tibial prosthesis extending through the elongated body, (iii) a medial connector formed in a medial side of the elongated body, and (iv) a lateral connector formed in a lateral side of the elongated body. The modular tibial cone augment also includes a medial lobe component having: (i) a body having a curved medial outer surface that tapers from a superior end to an inferior end thereof, (ii) a curved inner sidewall that corresponds in shape to the medial side of the elongated body of the central lobe component, and (iii) a medial connector formed in the curved inner sidewall which mates with the medial connector of the central lobe component so as to selectively lock the medial lobe component to the central lobe component. The modular tibial cone augment further includes a lateral lobe component having: (i) a body having a curved lateral outer surface that tapers from a superior end to an inferior end thereof, (ii) a curved inner sidewall that corresponds in shape to the lateral side of the elongated body of the central lobe component, and (iii) a lateral connector formed in the curved inner sidewall which mates with the lateral connector of the central lobe component so as to selectively lock the lateral lobe component to the central lobe component.

In an embodiment, the medial connector of the central lobe component and the medial connector of the medial lobe component define a dovetail joint. In a similar embodiment, the lateral connector of the central lobe component and the lateral connector of the lateral lobe component also define a dovetail joint.

In another embodiment, the medial connector of the central lobe component is embodied as a tapered slot formed in an outer surface of the elongated body, with the medial connector of the medial lobe component being embodied as a tapered tab extending outwardly from the curved inner sidewall. The tapered tab of the medial lobe component is configured to be received into the tapered slot of the central lobe component so as to selectively lock the medial lobe component to the central lobe component.

In another embodiment, the lateral connector of the central lobe component is embodied as a tapered slot formed in an outer surface of the elongated body, with the lateral connector of the lateral lobe component being embodied as a tapered tab extending outwardly from the curved inner sidewall. The tapered tab of the lateral lobe component is configured to be received into the tapered slot of the central lobe component so as to selectively lock the lateral lobe component to the central lobe component.

In an embodiment, a porous-metal coating is disposed on the outer surfaces of central lobe component, the medial lobe component, and the lateral lobe component.

The bore of the central lobe component is defined by a conically-shaped sidewall extending through the elongated body of the central lobe component, and the conically-shaped sidewall may have a number cement pockets formed therein.

According to another aspect of the disclosure, an orthopaedic knee implant includes a modular tibial cone augment configured to be implanted into a surgically-prepared cavity in a proximal end of a tibia of a patient. The modular tibial cone augment includes a central lobe component having: (i) a round elongated body, (ii) a bore configured to receive a stem of a revision tibial prosthesis extending through the elongated body, and (iii) a connector formed in a side of the elongated body. The modular tibial cone augment also includes a side lobe component having: (i) a body having a curved outer surface that tapers from a superior end to an inferior end thereof, (ii) a curved inner sidewall that corresponds in shape to the side of the elongated body of the central lobe component, and (iii) a connector formed in the curved inner sidewall which mates with the connector of the central lobe component so as to selectively lock the side lobe component to the central lobe component.

In an embodiment, the connector of the central lobe component and the connector of the side lobe component define a dovetail joint.

In another embodiment, the connector of the central lobe component is embodied as a tapered slot formed in an outer surface of the elongated body, with the connector of the side lobe component being embodied as a tapered tab extending outwardly from the curved inner sidewall. The tapered tab of the side lobe component is configured to be received into the tapered slot of the central lobe component so as to selectively lock the side lobe component to the central lobe component.

The side lobe component may be embodied as a medial lobe component or a lateral lobe component.

In an embodiment, a porous-metal coating is disposed on the outer surfaces of central lobe component and the side lobe component.

The bore of the central lobe component is defined by a conically-shaped sidewall extending through the elongated body of the central lobe component, and the conically-shaped sidewall may have a number cement pockets formed therein.

According to a further aspect of the disclosure, a method of surgically preparing a proximal end of a tibia of a patient includes determining a condition of bone tissue of the proximal end of the tibia of the patient, and thereafter forming a surgically-prepared cavity in the proximal end of the tibia of the tibia of a patient. A modular tibial cone augment is then assembled which corresponds to the shape of the surgically-prepared cavity by locking a side lobe component to a central lobe component, with the central lobe component having bore extending therethrough that is configured to receive a stem of a revision tibial prosthesis. The assembled modular tibial cone augment is then installed in the surgically-prepared cavity formed in the proximal end of the tibia.

In an embodiment, the side lobe component is embodied as a medial lobe component assembled to a medial side of the central lobe component.

In another embodiment, the side lobe component is embodied as a lateral lobe component assembled to a lateral side of the central lobe component.

In a further embodiment, the lobe component is embodied as a medial lobe component and a lateral lobe component. In such a case, the medial lobe component is assembled to a medial side of the central lobe component, and the lateral lobe component is assembled to a lateral side of the central lobe component.

BRIEF DESCRIPTION OF THE DRAWINGS

The detailed description particularly refers to the following figures, in which.

DETAILED DESCRIPTION OF THE DRAWINGS

Figure 1:
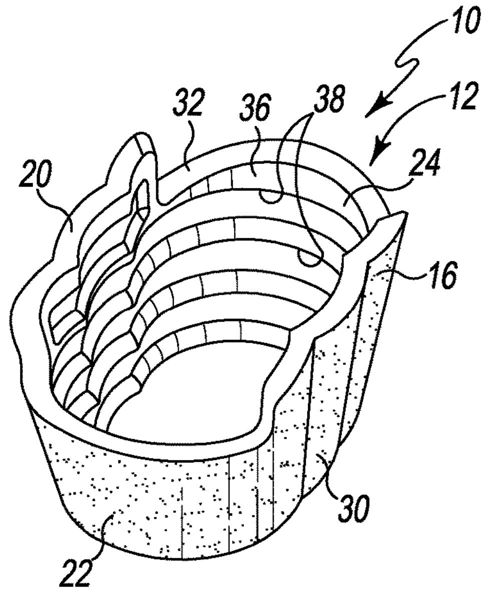
FIG. 1 is perspective view of tibial cone augment for use with a revision knee prosthesis.
Figure 2:
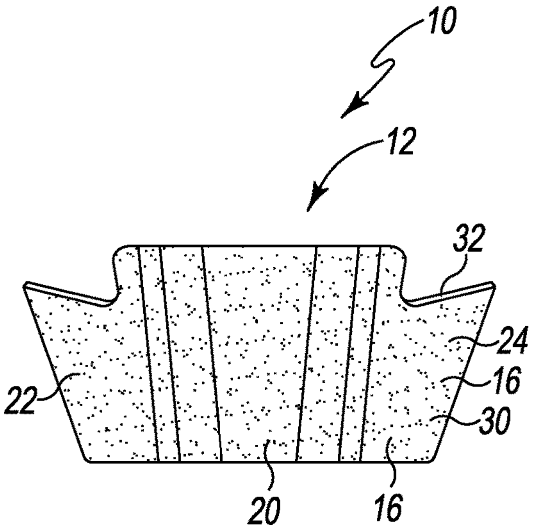
FIG. 2 is an anterior view of the tibial cone augment of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Various illustrative embodiments of knee cone augments are disclosed herein. Consistent with its usage in the art, what is meant herein by the term "cone augment" is an augment component that is not mechanically locked or otherwise secured to a revision knee prosthesis prior to implantation of the prosthesis, but rather is first separately implanted into the bone of the patient and thereafter secured to the subsequently implanted revision knee prosthesis, if secured to it at all, by use of an adhesive, such as bone cement. As a result, when installed in conjunction with the revision knee prosthesis, the cone augment does not physically contact the revision knee prosthesis, but rather is mechanically secured to it by the adhesive (e.g., bone cement), if secured to the revision knee prosthesis at all (e.g., the cone augment is not secured at all to a press-fit (i.e., cementless) stem component). As such, as used herein, a cone augment is distinct from a sleeve augment given sleeve augments are mechanically locked to a revision knee prosthesis prior to implantation of the prosthesis.

Referring now to FIGS. 1-11, an orthopaedic joint replacement system 10 includes a number of orthopaedic prosthetic components such as a tibial cone augment 12 and a number of orthopaedic surgical instruments such as a tibial surgical broach 14 (see, for example, FIGS. 5-7) for use in preparing the bone to receive one or more of the tibial cone augments 12. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic prosthetic components or implants, such as those shown in FIGS. 1-4.

The tibial cone augment 12 includes an elongated hollow body 16 having a central lobe section 20, a medial lobe section 22, and a lateral lobe section 24. It should be appreciated that although the tibial cone augment 12 is herein shown as a tri-lobe tibial augment (i.e., it has three lobe sections 20, 22, 24), the tibial cone augment 12 may be embodied as a bi-lobe tibial augment (i.e., having a central lobe section 20 and only one of the medial lobe section 22 or the lateral lobe section 24, but not both) or a concentric tibial augment (i.e., having a central lobe section 20, but neither the medial lobe section 22 nor the lateral lobe section 24). A bore 18 defined by the hollow body 16 in the central lobe section 20 is sized and shaped to receive a tibial stem component of a tibial revision prosthesis (not shown). Moreover, the size and shape of the bores 26, 28 defined by the hollow body 16 in the medial lobe section 22 and lateral lobe section 24, respectively, allow the position of the tibial stem component of the tibial revision prosthesis to be offset in the medial/lateral direction from the central lobe section as needed to fit the needs of a given surgical installation. Moreover, the bores 18, 26, 28 defined by the hollow body 16 allow for receipt of structures on the inferior side of a revision tibial tray such as one or more keels.

The body 16 of the tibial cone augment 12 is illustratively embodied as a solid-metal base 32 having a porous-metal coating 30 disposed thereon. It should be appreciated that the porous-metal coating 30 could be a separately-applied coating such as Porocoat® Porous Coating which is commercially available from DePuy Synthes of Warsaw, Indiana. However, in the illustrative embodiment described herein, the porous-metal coating 30 is disposed on the solid-metal base 32 by virtue of being additively manufactured contemporaneously with the solid-metal base 32 so as to create a common, monolithic component of the two metal structures.

In one example, the porous-metal coating 30 may be made of a porous material as described in U.S. patent application Ser. No. 16/365,557, which was filed Mar. 26, 2019 and is assigned to the same assignee as the present disclosure, the disclosure of which is hereby incorporated by reference as if set forth in its entirety herein. Additive manufacturing processes can include, by way of example, powder bed fusion printing, such as melting and sintering, cold spray 3D printing, wire feed 3D printing, fused deposition 3D printing, extrusion 3D printing, liquid metal 3D printing, stereolithography 3D printing, binder jetting 3D printing, material jetting 3D printing, and the like.

In one example, the porous material of the porous-metal coating 30 may be defined by a porous three-dimensional structure that includes a plurality of connected unit cells. Each unit cell may define a unit cell structure that includes a plurality of lattice struts that define an outer geometric structure and a plurality of internal struts that define a plurality of internal geometric structures that are disposed within the outer geometric structure. In one example, the outer geometric structure may be a rhombic dodecahedron, and the inner geometric structures may be a rhombic trigonal trapezohedron. It should be appreciated that such geometric structures may be varied to fit the needs of a given design. Further, it should be appreciated that the unit cells that make up the porous-metal coating 30 may also have any suitable alternative geometry to fit the needs of a given design.

The porous material of the porous-metal coating 30 is formed from a metal powder. Illustratively, the metal powders may include, but are not limited to, titanium, titanium alloys, stainless steel, cobalt chrome alloys, tantalum, or niobium powders. The porous-metal coating 30 has a porosity suitable to facilitate bony ingrowth into the tibial cone augment 12 when it is implanted into the surgically-prepared proximal end of the patient's tibia.

In the illustrative embodiment described herein, the porous-metal coating 30 is additively manufactured directly onto the outer surfaces of the solid-metal base 32. In such an embodiment, the two structures—i.e., the solid-metal base 32 and the porous-metal coating 30—may be manufactured contemporaneously during a common additive manufacturing process. For example, the two structures may be manufactured contemporaneously in a single 3D printing operation that yields a common, monolithic metallic component including both structures. Alternatively, the porous-metal coating 30 could be manufactured as a separate component that is secured to the solid-metal base 32.

Figure 3:
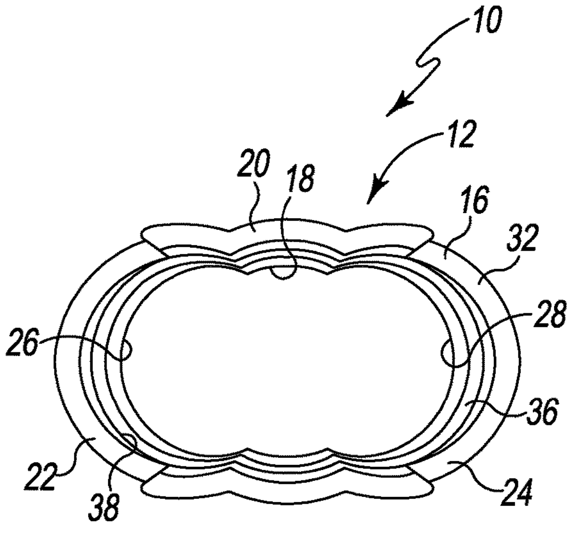
FIG. 3 is a superior view of the tibial cone augment of FIG. 1.
Figure 4:
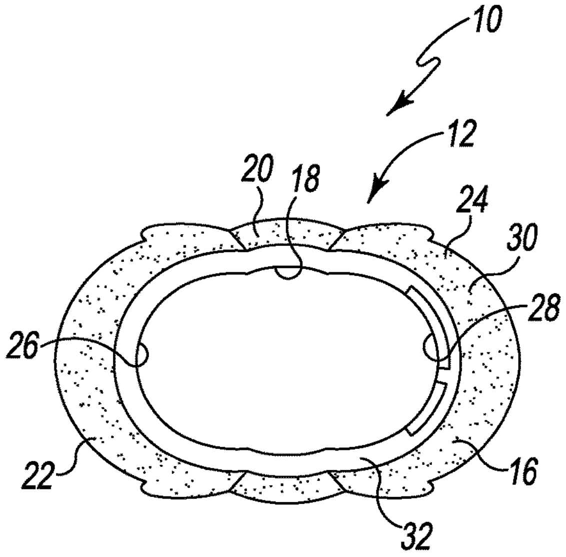
FIG. 4 is an inferior view of the tibial cone augment of FIG. 1.

As can be seen in FIGS. 1 and 3, the inner sidewall 36 that defines the bores 18, 26, 28 of the hollow body 16 have a number of cement pockets 38 formed therein. Bone cement is received into the cement pockets 38 to increase adhesion of the cement to the tibial cone augment 12 during implantation of the tibial revision prosthesis.

Figure 8:
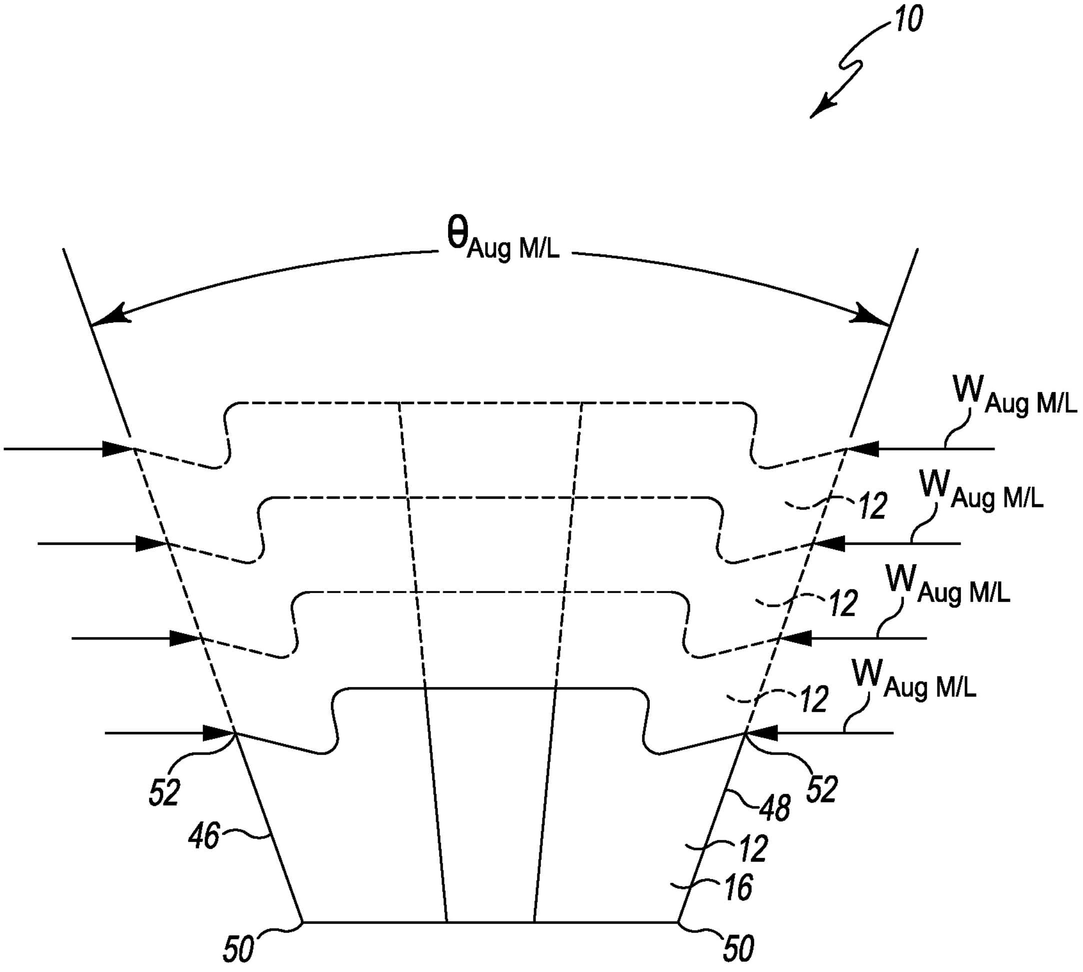
FIG. 8 is a diagrammatic view showing multiple sizes of the tibial cone augment of FIGS. 1-4 superimposed on one another, as viewed in the medial/lateral direction.
Figure 9:
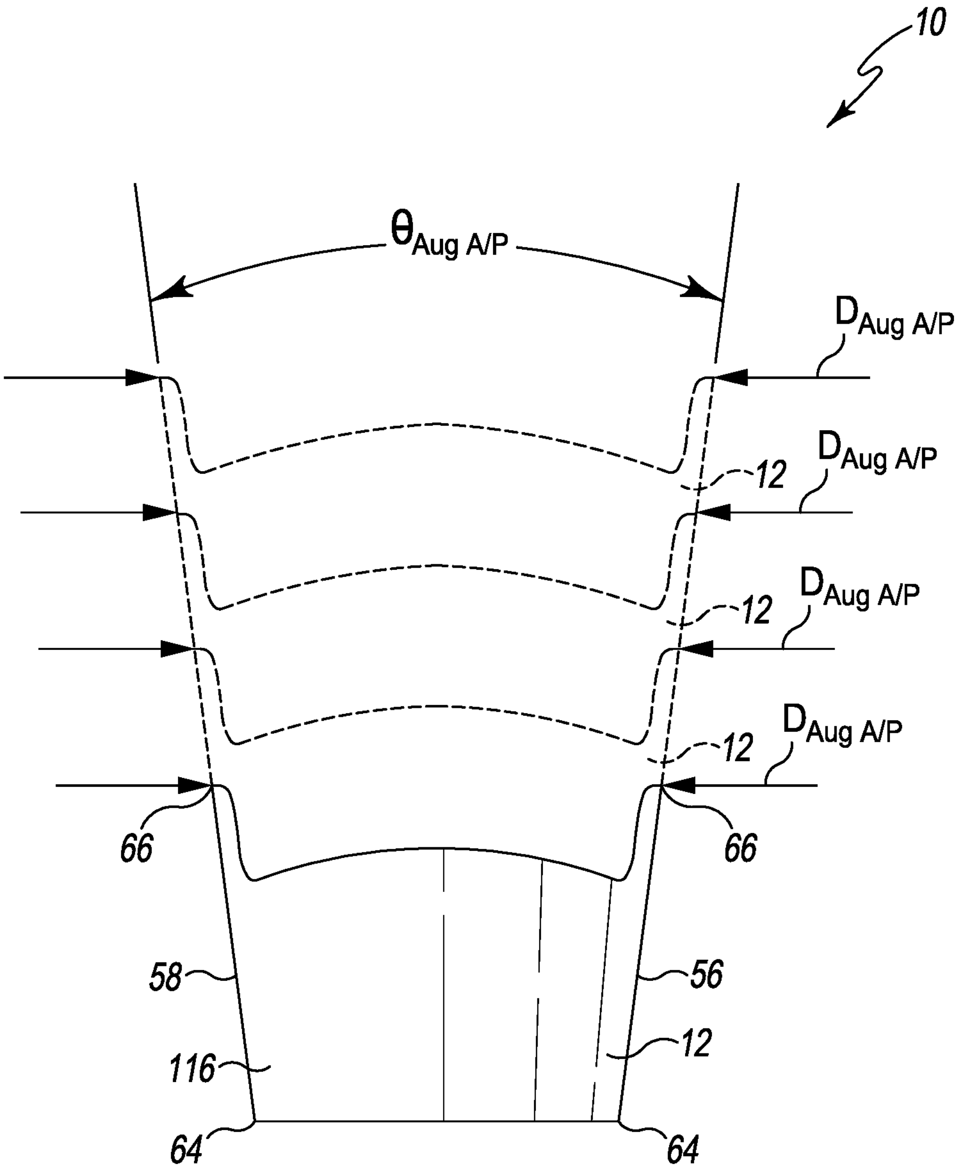
FIG. 9 is a diagrammatic view showing multiple sizes of the tibial cone augment of FIGS. 1-4 superimposed on one another, as viewed in the anterior/posterior direction.

As shown in FIGS. 8 and 9, the tibial cone augment 12 may be provided in a number of different configurations to fit the needs of a given patient's anatomy. In particular, the tibial cone augment 12 may be configured in various different sizes to conform to the patient's anatomy and/or accommodate a wide range of bone loss. In one illustrative embodiment, the tibial cone augment 12 may be provided in four different sizes (e.g., Sizes Small (S), Medium (M), Large (L), Extra Large (XL)). As shown in FIG. 8, the medial/lateral augment width of the body 16 changes as a function of the size of the tibial cone augment 12. As used herein, the term "medial/lateral augment width" refers to the width of the augment at its widest medial/lateral dimension. As can be seen in FIG. 8, the medial/lateral augment width ($W_{AugM/L}$) of the tibial cone augment 12 increases as the size of the tibial cone augment 12 increases. In other words, a Size M tibial cone augment 12 has a larger medial/lateral width than a Size S tibial cone augment 12, but a smaller medial/lateral width than a Size L (or Size XL) tibial cone augment 12.

However, as shown in FIG. 8, each of the differently-sized tibial cone augments 12 has a common taper angle in the medial/lateral direction (i.e., a common medial/lateral augment taper angle). In particular, the cone augment's "medial/lateral augment taper angle" is defined herein as the magnitude of the angle formed by the entirety of the medial-most edge 46 and the entirety of the lateral-most edge 48 of the augment. In other words, the cone augment's "medial/lateral augment taper angle" is defined as the magnitude of the angle formed by the medial-most edge 46 and the lateral-most edge 48 of the augment from the inferior-most end 50 of each edge 46, 48 to the superior-most end 52 of each edge 46, 48. As can be seen in FIG. 8, each of the differently-sized tibial cone augments 12 has a common medial/lateral augment taper angle ($\theta_{AugM/L}$). In the exemplary embodiment described herein, each of the differently-sized tibial cone augments 12 has a medial/lateral augment taper angle of 39° (i.e., $\theta_{AugM/L}$=39°).

As shown in FIG. 9, the anterior/posterior augment depth of the body 16 changes as a function of the size of the tibial cone augment 12. As used herein, the term "anterior/posterior augment depth" refers to the width of the augment at its widest anterior/posterior dimension. As can be seen in FIG. 9, the anterior/posterior augment depth ($D_{AugA/P}$) of the tibial cone augment 12 increases as the size of the tibial cone augment 12 increases. In other words, a Size M tibial cone augment 12 has a larger anterior/posterior augment depth than a Size S tibial cone augment 12, but a smaller anterior/posterior augment depth than a Size L (or Size XL) tibial cone augment 12.

However, as shown in FIG. 9, each of the differently-sized tibial cone augments 12 has a common taper angle in the anterior/posterior direction (i.e., a common anterior/posterior augment taper angle). In particular, the cone augment's "anterior/posterior augment taper angle" is defined herein as the magnitude of the angle formed by the entirety of the anterior-most edge 56 and the entirety of the posterior-most edge 58 of the augment. In other words, the cone augment's "anterior/posterior augment taper angle" is the magnitude of the angle formed by the anterior-most edge 56 and the lateral-most edge 58 of the cone augment from the inferior-most end 64 of each edge 56, 58 to the superior-most end 66 of each edge 56, 58. As can be seen in FIG. 9, each of the differently-sized tibial cone augments 12 has a common anterior/posterior augment taper angle ($\theta_{AugA/P}$). In the exemplary embodiment described herein, each of the differently-sized tibial cone augments 12 has an anterior/posterior augment taper angle of 14° (i.e., $\theta_{AugA/P}$=14°).

Figure 5:
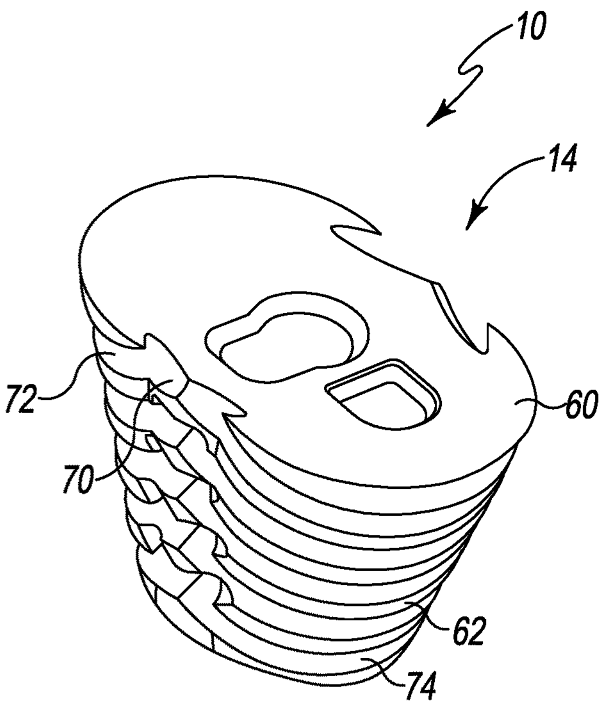
FIG. 5 is a perspective view of a tibial surgical broach for use in an orthopaedic surgical procedure to implant the tibial cone augment of FIGS. 1-4.
Figure 6:
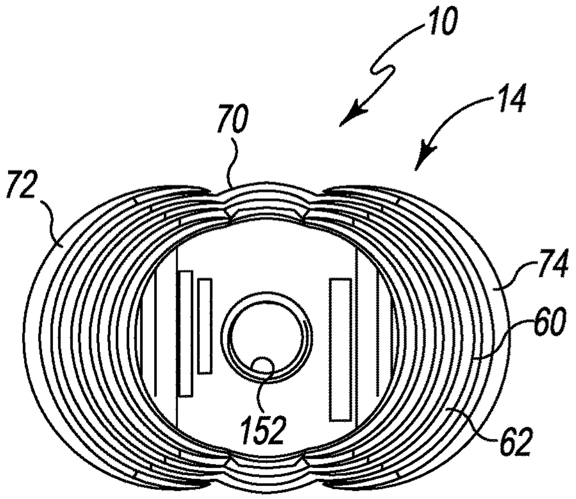
FIG. 6 is an inferior view of the tibial surgical broach of FIG. 5.
Figure 7:
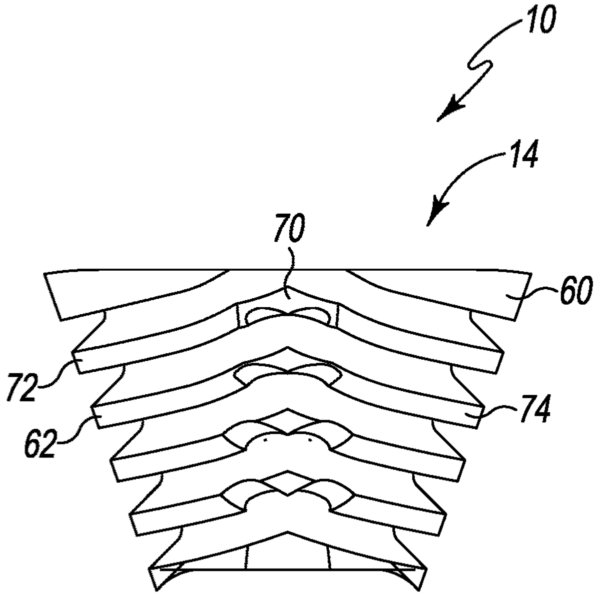
FIG. 7 is an anterior view of the tibial surgical broach of FIG. 5.

As shown in FIGS. 5-7, the tibial surgical broach 14 has a geometry that closely corresponds to the geometry of the tibial cone augment 12. In particular, the tibial surgical broach 14 has body 60 that includes a number of cutting teeth 62 that are configured to cut and remove bone tissue in a shape that corresponds to the shape of the tibial cone augment 12. As such, the cutting teeth 62 are arranged in a central lobe section 70, a medial lobe section 72, and a lateral lobe section 74. As with the tibial cone augment 12, it should be appreciated that although the tibial surgical broach 14 is herein shown as a tri-lobe tibial surgical broach (i.e., it has three lobe sections 70, 72, 74), the tibial surgical broach 14 may be embodied as a bi-lobe tibial surgical broach (i.e., having a central lobe section 70 and only one of the medial lobe section 72 or the lateral lobe section 74, but not both) or a concentric tibial surgical broach (i.e., having a central lobe section 70, but neither the medial lobe section 72 nor the lateral lobe section 74).

In the illustrative embodiment described herein, the tibial surgical broach 14 is constructed with stainless steel. Other suitable materials may be used to fit the needs of a given design of the broach 14.

Figure 10:
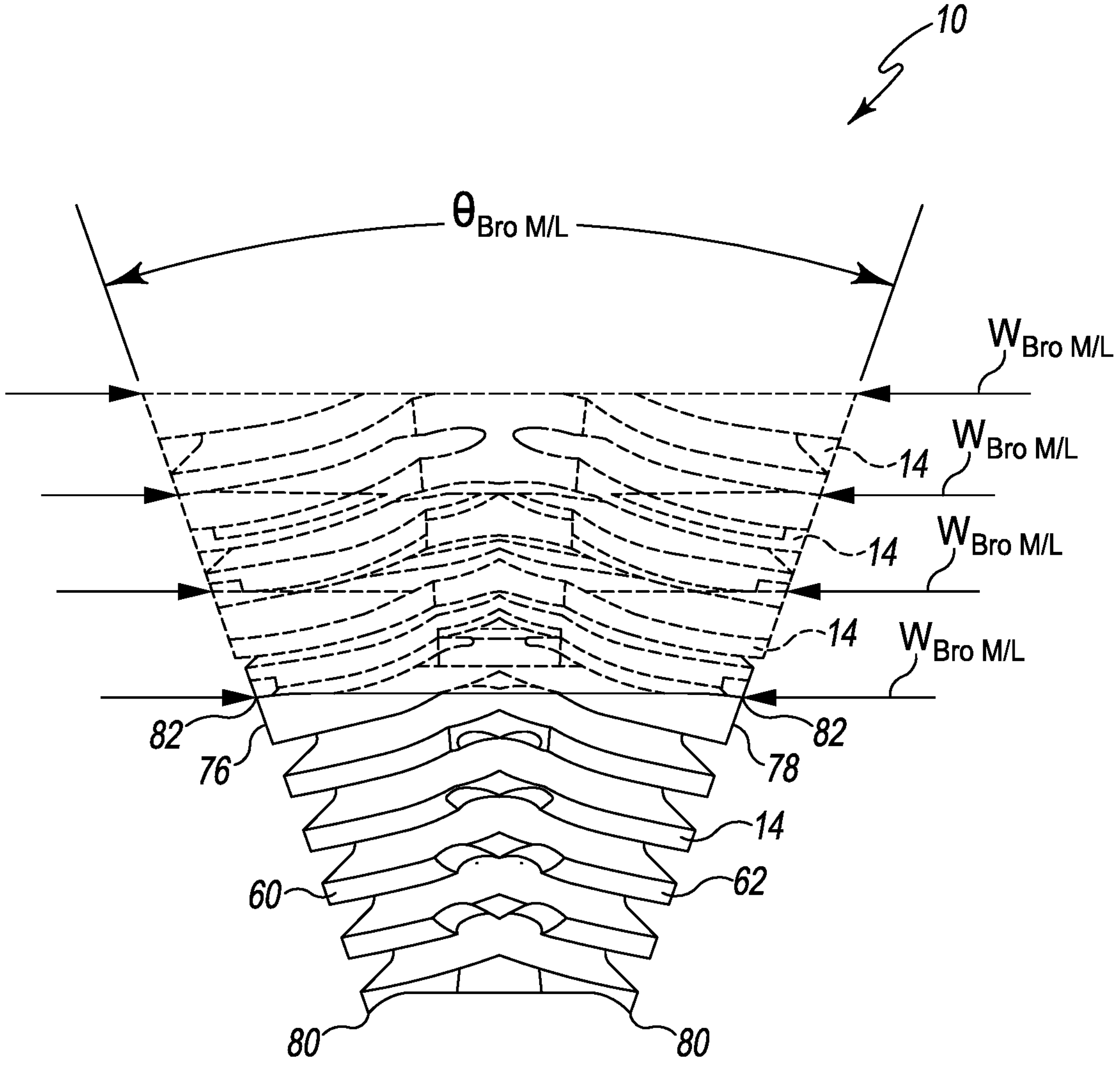
FIG. 10 is a diagrammatic view showing multiple sizes of the tibial surgical broach of FIGS. 5-7 superimposed on one another, as viewed in the medial/lateral direction.
Figure 11:
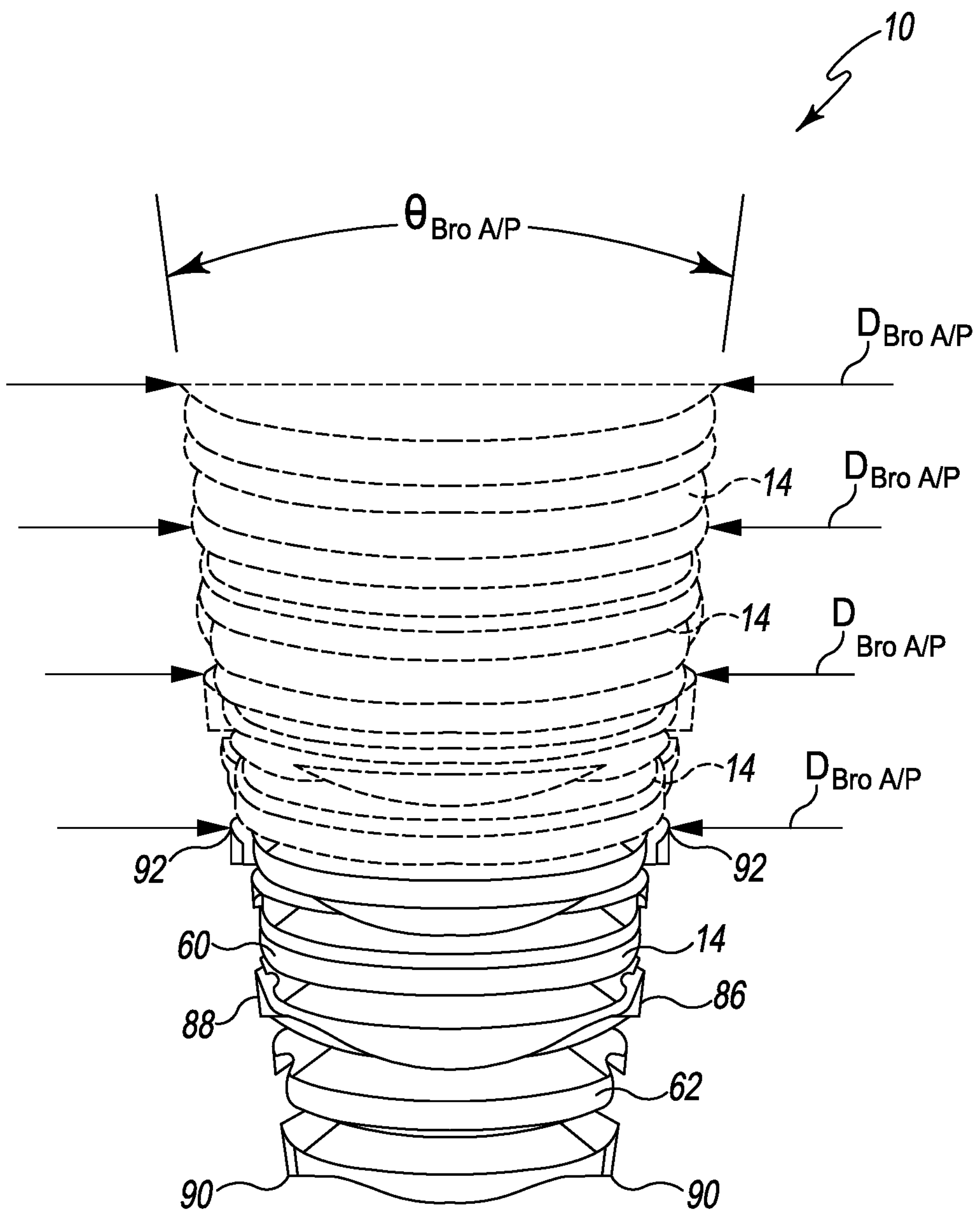
FIG. 11 is a diagrammatic view showing multiple sizes of the tibial surgical broach of FIGS. 5-7 superimposed on one another, as viewed in the anterior/posterior direction.

As shown in FIGS. 10 and 11, the tibial surgical broach 14 may be provided in a number of different configurations to correspond to the different configurations of the tibial cone augment 12. In particular, the tibial surgical broach 14 may be configured in various different sizes to conform to the sizes of the tibial cone augment 12. As such, in one illustrative embodiment, the tibial surgical broach 14 may be provided in four different sizes (e.g., Sizes Small (S), Medium (M), Large (L), Extra Large (XL)). As shown in FIG. 10, the medial/lateral broach width of the body 60 changes as a function of the size of the tibial surgical broach 14. As used herein, the term "medial/lateral broach width" refers to the width of the broach at its widest medial/lateral dimension. As can be seen in FIG. 10, the medial/lateral broach width ($W_{BroM/L}$) of the tibial surgical broach 14 increases as the size of the tibial surgical broach 14 increases. In other words, a Size M tibial surgical broach 14 has a larger medial/lateral broach width than a Size S tibial surgical broach 14, but a smaller medial/lateral broach width than a Size L (or XL) tibial surgical broach 14.

However, like the tibial cone augment 12 and as shown in FIG. 10, each of the differently-sized tibial surgical broaches 14 has a common taper angle in the medial/lateral direction (i.e., a common medial/lateral broach taper angle). In particular, the surgical broach's "medial/lateral broach taper angle" is defined herein as the magnitude of the angle formed by the entirety of an imaginary line extending along and connecting the medial-most edges 76 of the broach's individual cutting teeth 62 and the entirety of an imaginary line extending along and connecting the lateral-most edges 78 of the broach's individual cutting teeth 62. In other words, the surgical broach's "medial/lateral broach taper angle" is the magnitude of the angle formed by the imaginary line extending along and connecting the medial-most edges 76 of the broach's individual cutting teeth 62 and the imaginary line extending along and connecting the lateral-most edges 78 of the broach's individual cutting teeth 62 from the distal-most end 80 of each imaginary line to the proximal-most end 82 of each imaginary line.

Moreover, the medial/lateral broach taper angle of the broach 14 is the same as the medial/lateral augment taper angle of the tibial cone augment 12. Specifically, the medial/lateral taper angle of the broach 14 matches the medial/lateral taper angle of the augment 12. As such and as can be seen in FIGS. 8 and 10, each of the differently-sized tibial surgical broaches 14 has a common medial/lateral broach taper angle ($\theta_{BroM/L}$), which is the same as the medial/lateral augment taper angle ($\theta_{AugM/L}$) common to each of the tibial cone augments 12. In the exemplary embodiment described herein, each of the differently-sized tibial surgical broaches has a medial/lateral broach taper angle of 39° (i.e., $\theta_{BroM/L}$=39°).

As shown in FIG. 11, the anterior/posterior broach depth of the body 60 changes as a function of the size of the tibial surgical broach 14. As used herein, the term "anterior/posterior broach depth" refers to the width of the broach at its widest anterior/posterior dimension. As can be seen in FIG. 11, the anterior/posterior broach depth ($D_{BroA/P}$) of the tibial surgical broach 14 increases as the size of the tibial surgical broach 14 increases. In other words, a Size M tibial surgical broach 14 has a larger anterior/posterior broach depth than a Size S tibial surgical broach 14, but a smaller anterior/posterior augment depth than a Size L (or Size XL) tibial surgical broach 14.

However, as shown in FIG. 11, each of the differently-sized tibial surgical broaches 14 has a common taper angle in the anterior/posterior direction (i.e., a common anterior/posterior broach taper angle). In particular, the tibial surgical broach's "anterior/posterior broach taper angle" is defined herein as the magnitude of the angle formed by the entirety of an imaginary line extending along and connecting the anterior-most edges 86 of the broach's individual cutting teeth 62 and the entirety of an imaginary line extending along and connecting the posterior-most edges 88 of the broach's individual cutting teeth 62. In other words, the surgical broach's "anterior/posterior broach taper angle" is the magnitude of the angle formed by the imaginary line extending along and connecting the anterior-most edges 86 of the broach's individual cutting teeth 62 and the imaginary line extending along and connecting the posterior-most edges 88 of the broach's individual cutting teeth 62 from the distal-most end 90 of each imaginary line to the proximal-most end 92 of each imaginary line.

Moreover, the anterior/posterior broach taper angle of the broach 14 is the same as the anterior/posterior augment taper angle of the tibial augment component 12. Specifically, the anterior/posterior taper angle of the broach 14 matches the anterior/posterior taper angle of the augment 12. As such and as can be seen in FIGS. 9 and 11, each of the differently-sized tibial surgical broach's 14 has a common anterior/posterior broach taper angle ($\theta_{BroA/P}$), which is the same as the anterior/posterior augment taper angle ($\theta_{AugA/P}$) common to each of the tibial cone augments 12. In the exemplary embodiment described herein, each of the differently-sized tibial surgical broaches has an anterior/posterior broach taper angle of 14° (i.e., $\theta_{BroA/P}$=) 14°).

Referring now to FIGS. 12-21, the orthopaedic joint replacement system 10 also includes a femoral cone augment 112 and a femoral surgical broach 114 for use in preparing the bone to receive one of the femoral cone augments 112. The femoral cone augment 112 includes an elongated hollow body 116 that is open on its anterior side. The bore 118 defined by the hollow body 116 is sized and shaped to receive a femoral stem component of a femoral revision prosthesis (not shown). Moreover, the size and shape of the bore 118 allow the position of the femoral stem component of the femoral revision prosthesis to be offset in the medial/lateral direction from the center of the augment 112 as needed to fit the needs of a given surgical installation. Moreover, the body 116 has a cutout 120 formed in the posterior side of the femoral cone augment 112. The cutout 120 provides clearance for the box of the revision femoral component.

Like the body 16 of the tibial cone component 12, the body 116 of the femoral cone augment 112 is illustratively embodied as a solid-metal base 132 having a porous-metal coating 130 disposed thereon. The solid-metal base 132 and the porous-metal coating 130 may be embodied and manufactured in a similar manner as to the solid-metal base 32 and the porous metal coating 30 discussed above in regard to the tibial cone component 12, with all such features, methods, starting materials, and alternatives not being repeated herein for purposes of brevity. In the illustrative embodiment described herein, like as was described above in regard to the tibial cone augment 12, the porous-metal coating 130 is disposed on the solid-metal base 132 of the femoral cone augment 112 by virtue of being additively manufactured contemporaneously with the solid-metal base 132 so as to create a common, monolithic component of the two metal structures.

Figure 12:
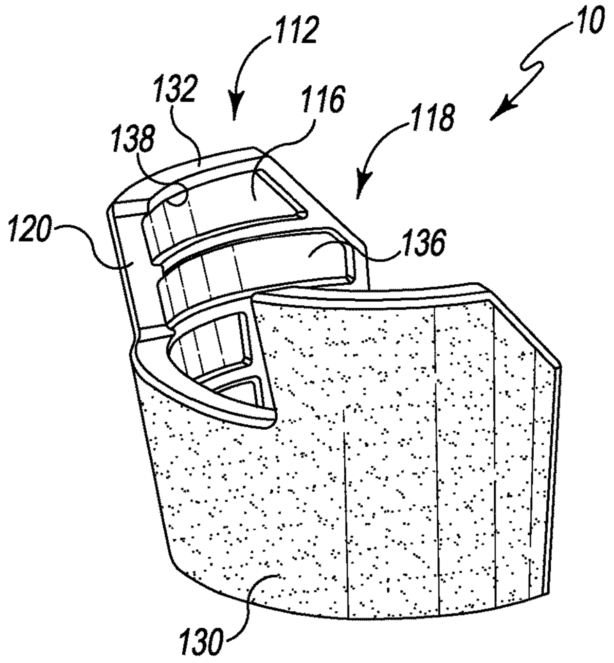
FIG. 12 is perspective view of femoral cone augment for use with a revision knee prosthesis.
Figure 13:
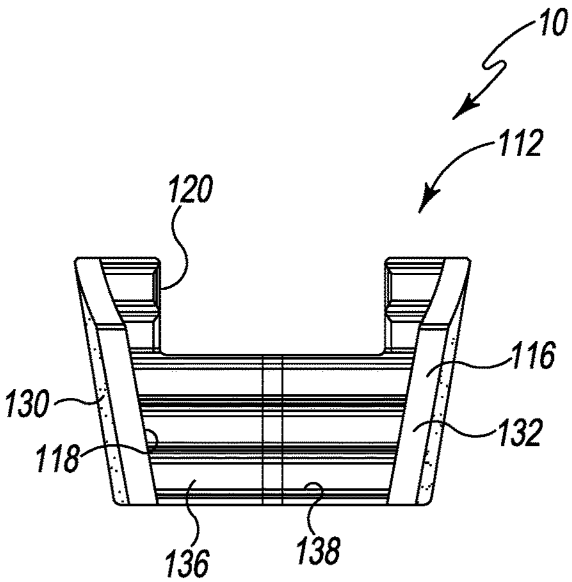
FIG. 13 is an anterior view of the femoral cone augment of FIG. 12.
Figure 14:
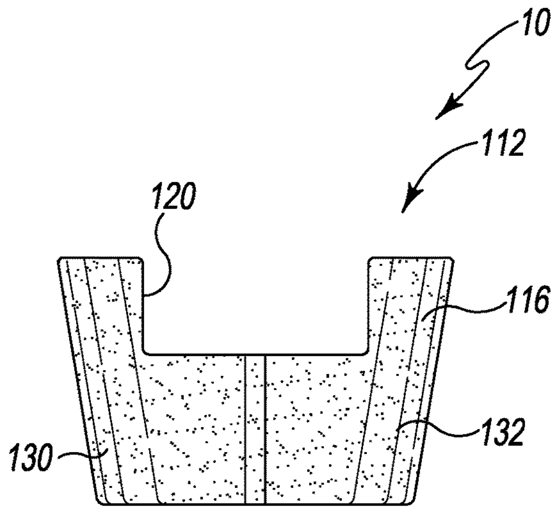
FIG. 14 is a posterior view of the femoral cone augment of FIG. 12.

As can be seen in FIGS. 12 and 13, the inner sidewall 136 that defines the bore 118 of the hollow body 116 have a number of cement pockets 138 formed therein. Bone cement is received into the cement pockets 138 to increase adhesion of the cement to the femoral cone augment 112 during implantation of the femoral revision prosthesis.

Figure 18:
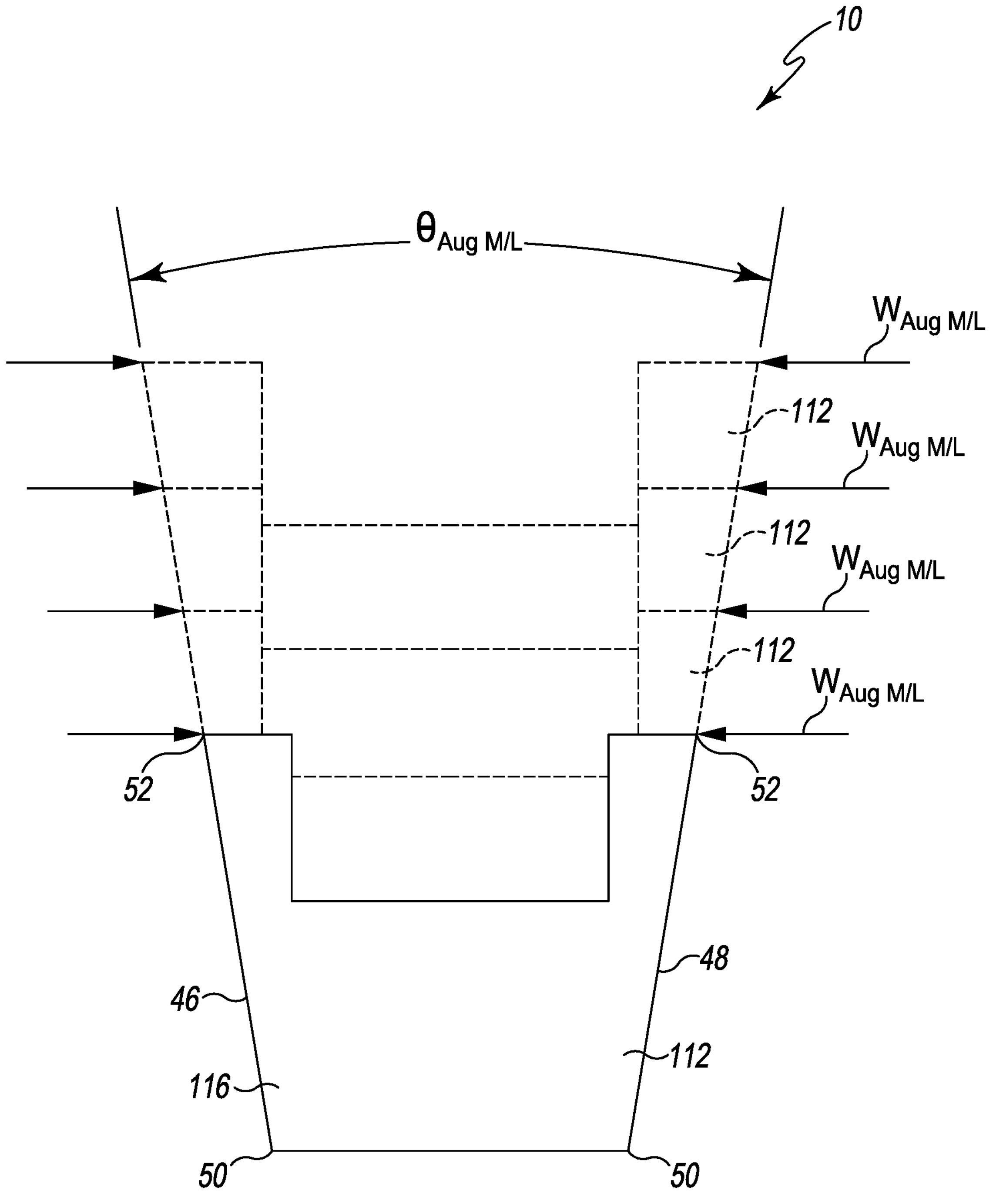
FIG. 18 is a diagrammatic view showing multiple sizes of the femoral cone augment of FIGS. 12-14 superimposed on one another, as viewed in the medial/lateral direction.
Figure 19:
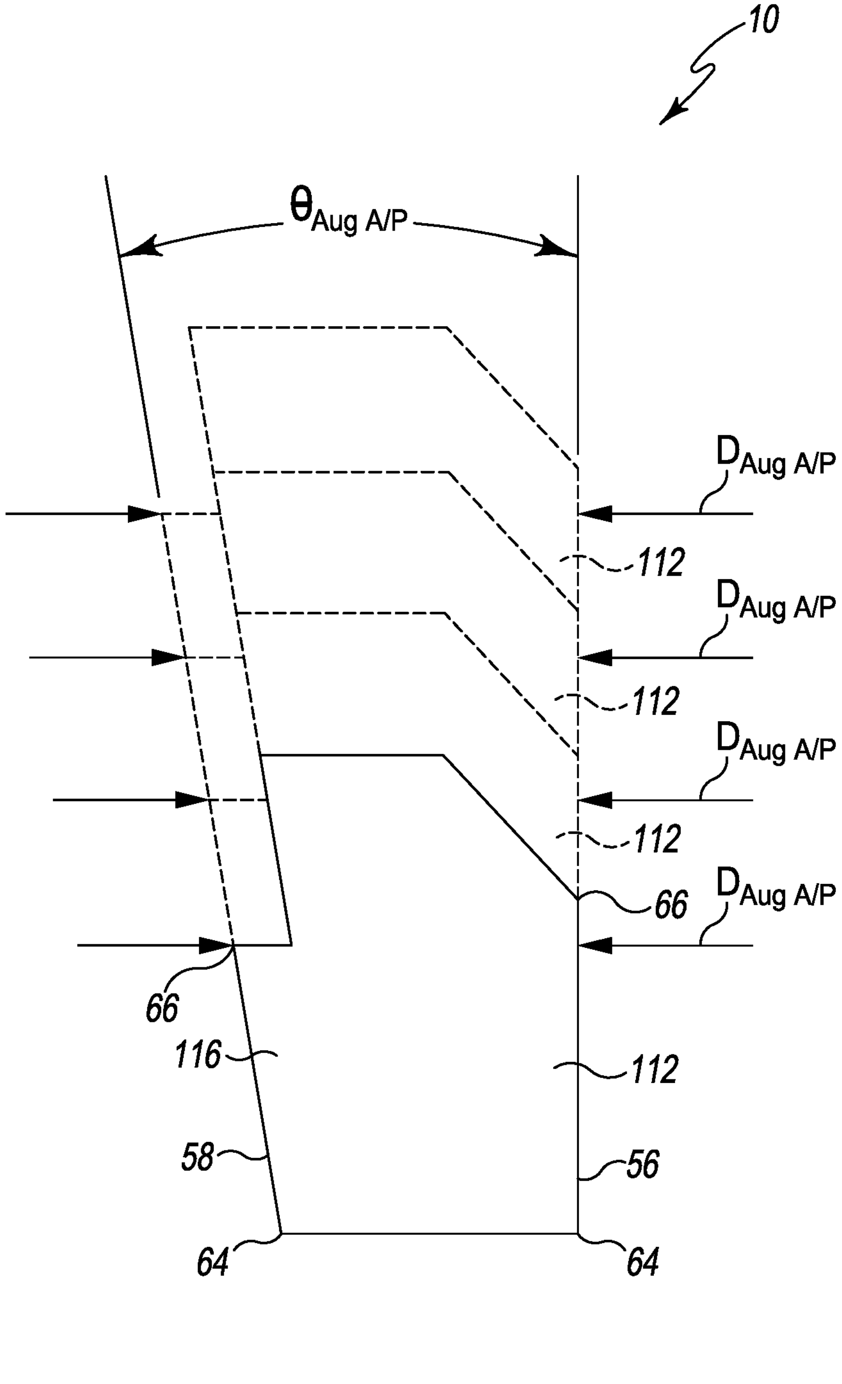
FIG. 19 is a diagrammatic view showing multiple sizes of the femoral cone augment of FIGS. 12-14 superimposed on one another, as viewed in the anterior/posterior direction.

As shown in FIGS. 18 and 19, like the tibial cone augment 12, the femoral cone augment 112 may be provided in a number of different configurations to fit the needs of a given patient's anatomy. In particular, the femoral cone augment 112 may be configured in various different sizes to conform to the patient's anatomy and/or accommodate a wide range of bone loss. In one illustrative embodiment, the femoral cone augment 112 may be provided in four different sizes (e.g., Sizes Small (S), Medium (M), Large (L), Extra Large (XL)), although other sizes (e.g., Size Double Extra Large (XXL)) could also be provided to fit the needs of a given design of the orthopaedic joint replacement system 10. As shown in FIG. 18, the medial/lateral augment width of the body 116 changes as a function of the size of the femoral cone augment 112. As can be seen in FIG. 18, the medial/lateral augment width ($W_{AugM/L}$) of the femoral cone augment 112 increases as the size of the femoral cone augment 112 increases. In other words, a Size M femoral cone augment 112 has a larger medial/lateral width than a Size S femoral cone augment 112, but a smaller medial/lateral width than a Size L (or Size XL) femoral cone augment 112.

However, as also shown in FIG. 18, like the tibial cone augment 12, each of the differently-sized femoral cone augments 112 has a common taper angle in the medial/lateral direction (i.e., a common medial/lateral augment taper angle). Specifically, each of the differently-sized femoral cone augments 112 has a common medial/lateral augment taper angle ($\theta_{AugM/L}$). In the exemplary embodiment described herein, each of the differently-sized femoral cone augments 112 has a medial/lateral augment taper angle of 19° (i.e., $\theta_{AugM/L}$=19°).

As shown in FIG. 19, the anterior/posterior augment depth of the body 116 changes as a function of the size of the femoral cone augment 112. In particular, the anterior/posterior augment depth ($D_{AugA/P}$) of the femoral cone augment 112 increases as the size of the femoral cone augment 112 increases. In other words, a Size M femoral cone augment 112 has a larger anterior/posterior augment depth than a Size S femoral cone augment 112, but a smaller anterior/posterior augment depth than a Size L (or Size XL) femoral cone augment 112.

However, as shown in FIG. 19, each of the differently-sized femoral cone augments 112 has a common taper angle in the anterior/posterior direction (i.e., a common anterior/posterior augment taper angle). Specifically, each of the differently-sized femoral cone augments 112 has a common anterior/posterior augment taper angle ($\theta_{AugA/P}$). In the exemplary embodiment described herein, each of the differently-sized femoral cone augments 112 has an anterior/posterior augment taper angle of 9.5° (i.e., $\theta_{AugA/P}$=9.5°).

Figure 15:
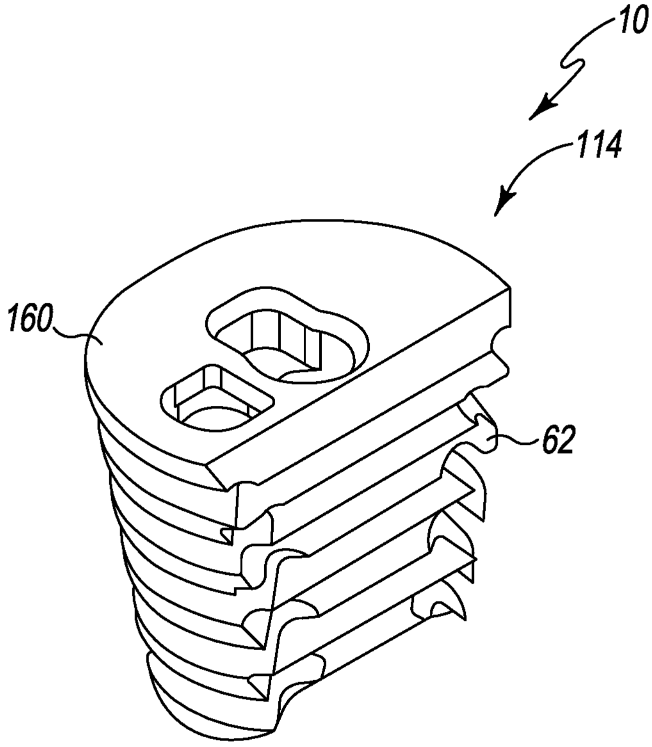
FIG. 15 is a perspective view of a femoral surgical broach for use in an orthopaedic surgical procedure to implant the femoral cone augment of FIGS. 12-14.
Figure 16:
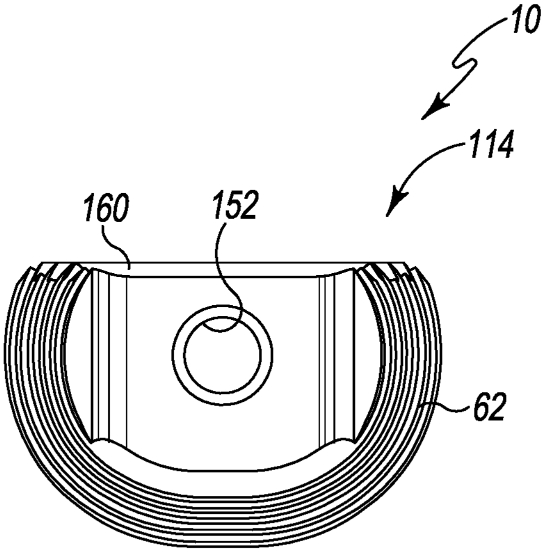
FIG. 16 is an inferior view of the femoral surgical broach of FIG. 15.
Figure 17:
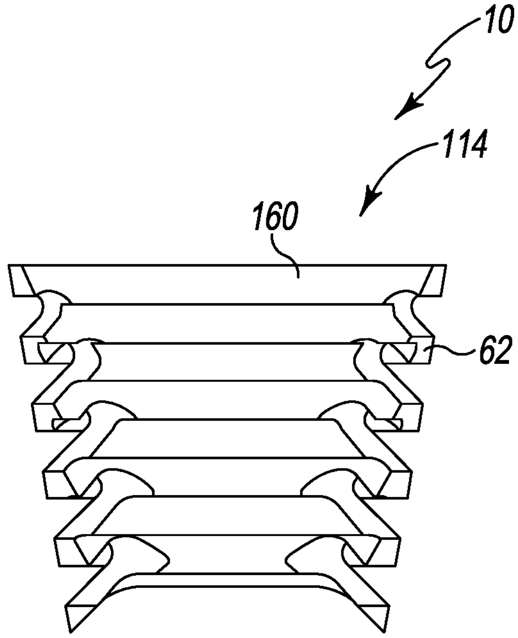
FIG. 17 is an anterior view of the femoral surgical broach of FIG. 15.

As shown in FIGS. 15-17, the femoral surgical broach 114 has a geometry that closely corresponds to the geometry of the femoral cone augment 112. In particular, the femoral surgical broach 114 has body 160 that includes a number of cutting teeth 62 that are configured to cut bone tissue in a shape that corresponds to the shape of the femoral cone augment 112. Like the tibial surgical broach 14, in the illustrative embodiment described herein, the femoral surgical broach 114 is constructed with stainless steel. Other suitable materials may be used to fit the needs of a given design of the broach 114.

Figure 20:
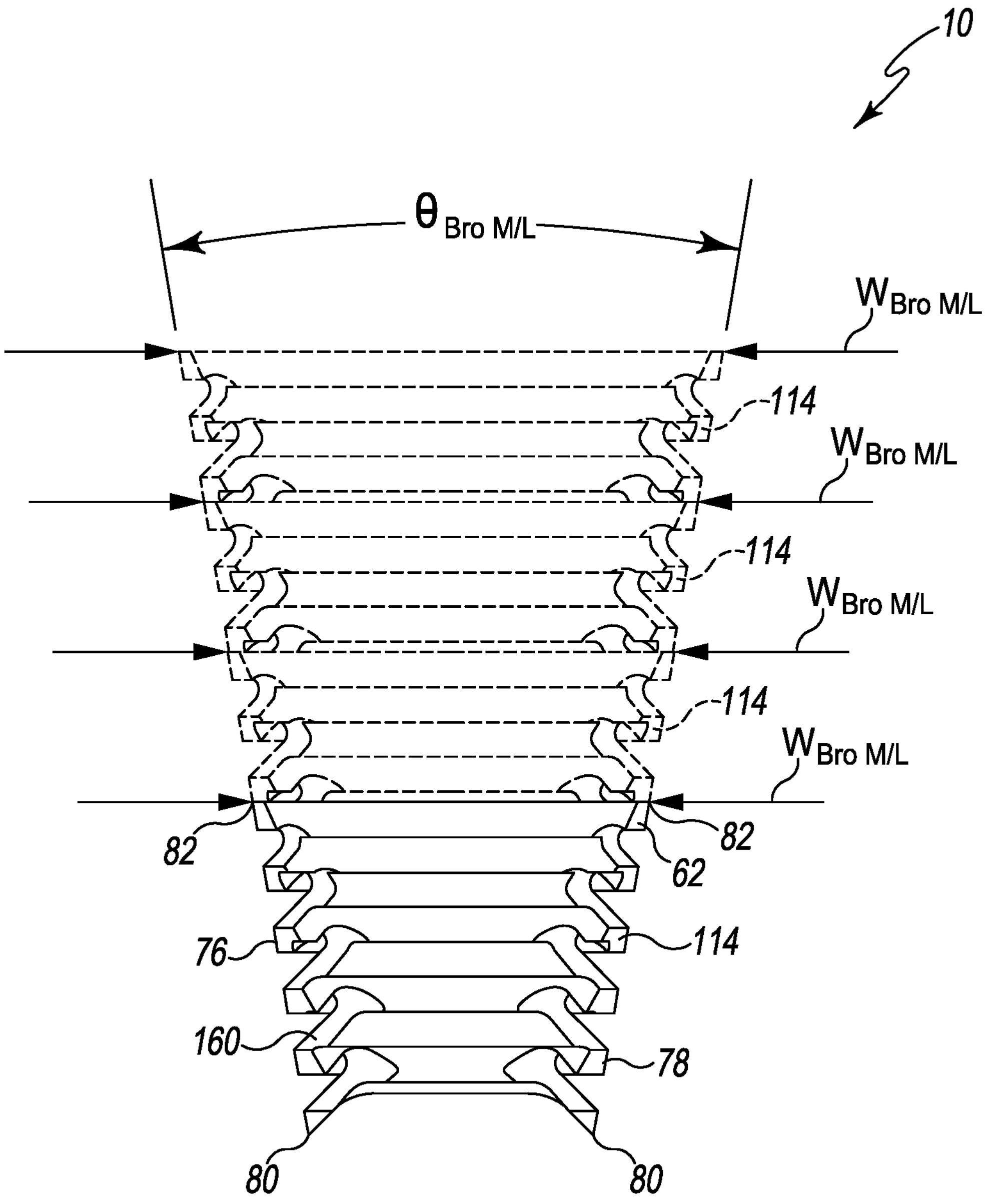
FIG. 20 is a diagrammatic view showing multiple sizes of the femoral surgical broach of FIGS. 15-17 superimposed on one another, as viewed in the medial/lateral direction.
Figure 21:
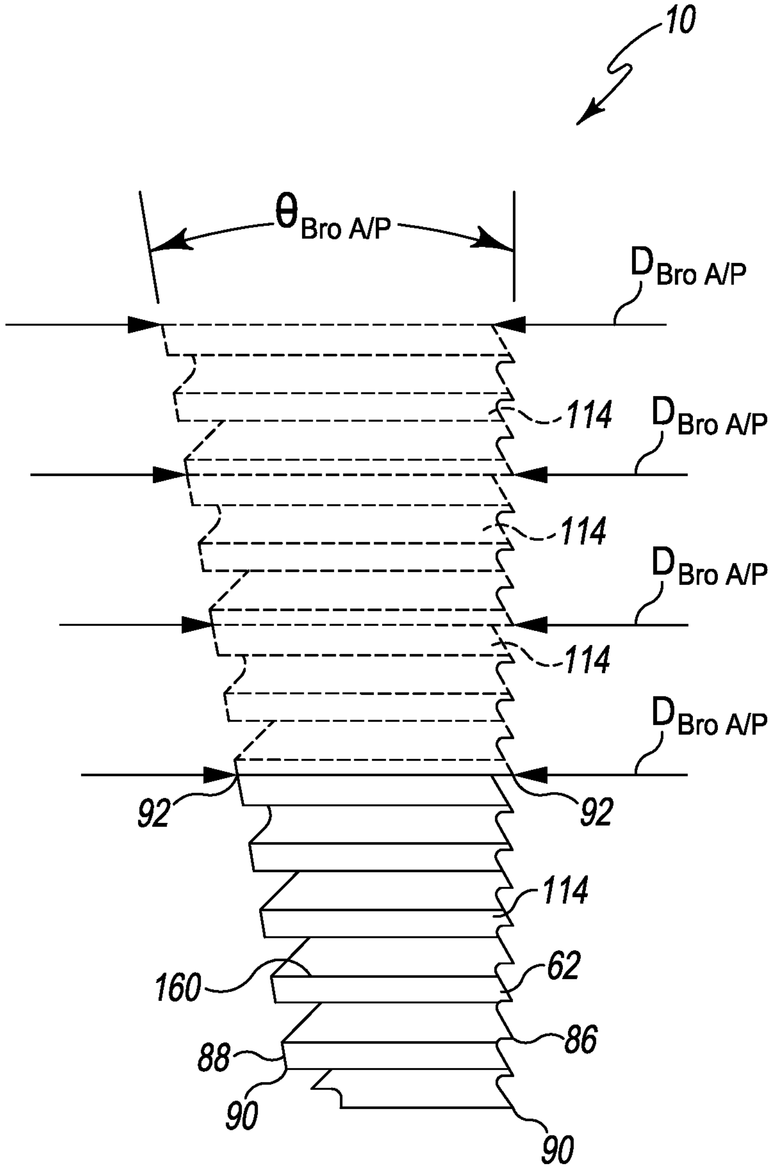
FIG. 21 is a diagrammatic view showing multiple sizes of the femoral surgical broach of FIGS. 15-17 superimposed on one another, as viewed in the anterior/posterior direction.

As shown in FIGS. 20 and 21, the femoral surgical broach 114 may be provided in a number of different configurations to correspond to the different configurations of the femoral cone augment 112. In particular, the femoral surgical broach 114 may be configured in various different sizes to conform to the sizes of the femoral cone augment 112. As such, in one illustrative embodiment, the femoral surgical broach 114 may be provided in four different sizes (e.g., Sizes Small (S), Medium (M), Large (L), Extra Large (XL)), although additional sizes of the femoral surgical broach 114 (e.g., Size Double Extra Large (XXL)) could also be provided if the femoral cone augment 112 is provided in such additional sizes. As shown in FIG. 20, the medial/lateral broach width of the body 160 changes as a function of the size of the femoral surgical broach 114. Specifically, as can be seen in FIG. 20, the medial/lateral broach width ($W_{BroM/L}$) of the femoral surgical broach 114 increases as the size of the femoral surgical broach 114 increases. In other words, a Size M femoral surgical broach 114 has a larger medial/lateral broach width than a Size S femoral surgical broach 114, but a smaller medial/lateral broach width than a Size L (or Size XL) femoral surgical broach 114.

However, like the femoral cone augment 112 and as shown in FIG. 20, each of the differently-sized femoral surgical broaches 114 has a common taper angle in the medial/lateral direction (i.e., a common medial/lateral broach taper angle). Moreover, the medial/lateral broach taper angle of the broach 114 is the same as the medial/lateral augment taper angle of the femoral cone augment 112. Specifically, the medial/later taper angle of the broach 114 matches the medial/lateral taper angle of the augment 112. As such and as can be seen in FIGS. 18 and 20, each of the differently-sized tibial surgical broaches 114 has a common medial/lateral broach taper angle ($\theta_{BroM/L}$), which is the same as the medial/lateral augment taper angle ($\theta_{AugM/L}$) common to each of the femoral cone augments 112. In the exemplary embodiment described herein, each of the differently-sized femoral surgical broaches 114 has a medial/lateral broach taper angle of 19° (i.e., $\theta_{BroM/L}$=19°).

As shown in FIG. 21, the anterior/posterior broach depth of the body 160 changes as a function of the size of the femoral surgical broach 114. Specifically, the anterior/posterior broach depth ($D_{BroA/P}$) of the femoral surgical broach 114 increases as the size of the femoral surgical broach 114 increases. In other words, a Size M femoral surgical broach 114 has a larger anterior/posterior broach depth than a Size S femoral surgical broach 114, but a smaller anterior/posterior augment depth than a Size L (or Size XL) femoral surgical broach 114.

However, as shown in FIG. 21, each of the differently-sized femoral surgical broaches 114 has a common taper angle in the anterior/posterior direction (i.e., a common anterior/posterior broach taper angle). Moreover, the anterior/posterior broach taper angle of the broach 114 is the same as the anterior/posterior augment taper angle of the femoral cone augment 112. Specifically, the anterior/posterior taper angle of the broach 114 matches the anterior/posterior taper angle of the augment 112. As such and as can be seen in FIGS. 19 and 21, each of the differently-sized tibial surgical broaches 114 has a common anterior/posterior broach taper angle ($\theta_{BroA/P}$), which is the same as the anterior/posterior augment taper angle ($\theta_{AugA/P}$) common to each of the femoral cone augments 112. In the exemplary embodiment described herein, each of the differently-sized femoral surgical broaches 114 has an anterior/posterior broach taper angle of 9.5° (i.e., $\theta_{BroA/P}$=9.5°).

As described above, the geometry of the surgical broaches 14, 114 closely corresponds to the geometry of the cone augments 12, 112. Specifically, a common medial/lateral taper angle and a common anterior/posterior taper angle is used between all the different sizes of the tibial surgical broaches 12 and the tibial cone augments 14, with a common medial/lateral taper angle and a common anterior/posterior taper angle also being used between all the different sizes of the femoral surgical broaches 112 and the femoral cone augments 114. Such an arrangement provides for enhanced ease of use during performance of an orthopaedic surgical procedure given it provides for enhanced flexibly in the intra-operative decision making by the surgeon. For example, if during the trialing process, the surgeon determines that the patient's bone was over prepped (i.e., a larger bone cavity was created than needed), the surgeon can simply substitute a larger cone augment than originally planned since the augments all "grow" along the same taper angles throughout the range of sizes. Similarly, in the case of when the surgeon determines that the patient's bone was under prepped (i.e., a smaller bone cavity was created than needed), the surgeon can simply broach the cavity with the next size up broach. Alternatively, the surgeon can also substitute a smaller cone augment than originally planned and simply allow the smaller cone augment to sit a bit deeper in the prepared cavity since the cavity has been broached to common taper angles relative to the entire range of augment sizes. Use of a smaller cone augment sitting deeper in the cavity may be preferred over re-broaching the cavity to a larger size in the case of when the larger broach might be less than ideal due to the anatomy of the patient or the magnitude of bone available in one direction or the other (e.g., the amount of bone available in the anterior/posterior direction may be limited even though ample bone exists for the larger broach in the medial/lateral direction).

As will be described below in greater detail, the surgical broaches 14, 114 are used in combination with a stem trial component 150 to surgically prepare the proximal end of a patient's tibia (in the case of the tibial surgical broach 14) or the distal end of the patient's femur (in the case of the femoral surgical broach 114). As used herein, the term "stem trial component" refers to is an orthopaedic surgical instrument for use by a surgeon in trialing or otherwise assessing the fit of an intramedullary stem component during performance an orthopaedic surgical procedure. As such, it should be appreciated that, as used herein, the term "stem trial component" is distinct from orthopaedic implants or prostheses that are surgically implanted in the body of the patient or other orthopaedic surgical instruments (such as canal reamers, intramedullary rods, etcetera) that are used to perform other functions during an orthopaedic surgical procedure.

As can be seen in FIGS. 6 and 16, the surgical broaches 14, 114 have a threaded bore 152 formed in their respective distal ends 154. The threaded bore 152 is sized to receive a threaded post 154 formed in the proximal end 156 of the stem trial component 150 (the threaded post 154 can be seen, for example, in FIG. 27) so as to selectively secure the stem trial component 150 to the broach 14, 114. In such a way, and as discussed below in more detail, the stem trial component 150 may be used as a guide instrument during use of the broach 14, 114. In doing so, the stem trial component 150 provides an enhanced and simplified approach to guiding the broaching process relative to use of heretofore designed systems which can require complex apparatus to be assembled to the bone.

Figure 22:
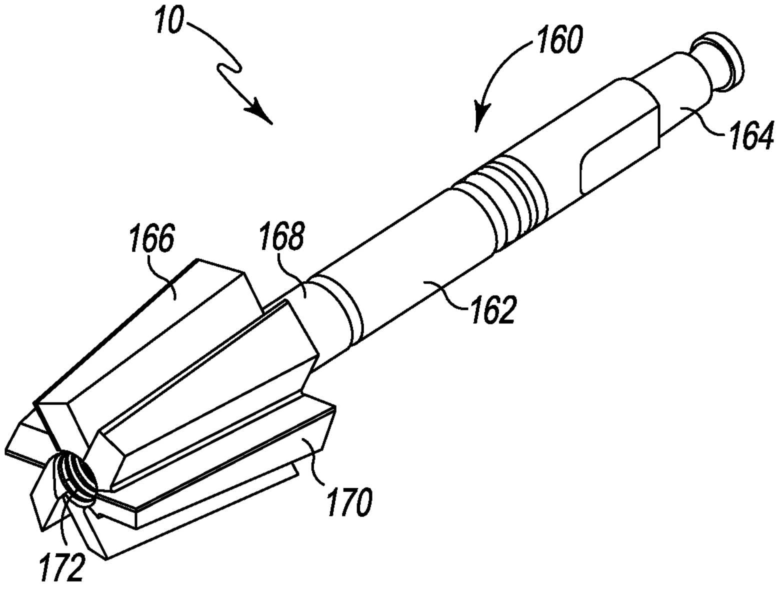
FIG. 22 is a perspective view of a cone reamer.
Figure 23:
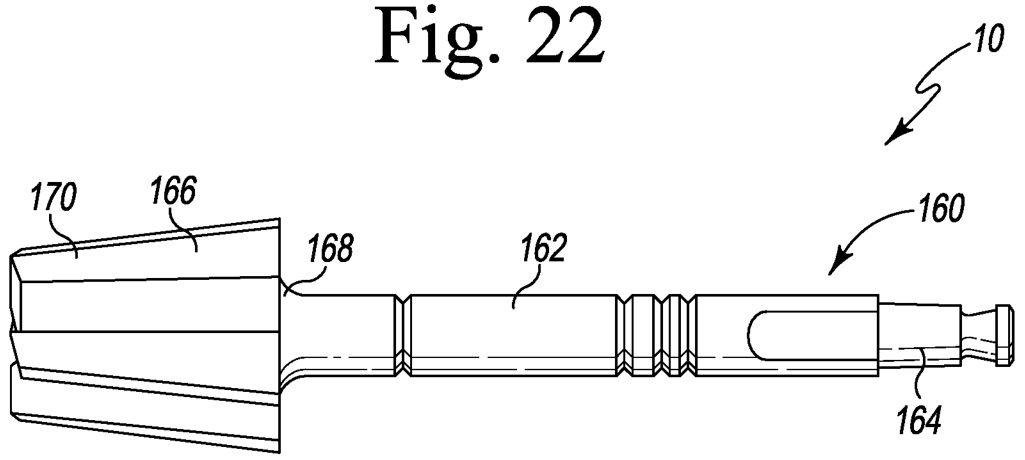
FIG. 23 is a side view of the cone reamer of FIG. 22.
Figure 24:
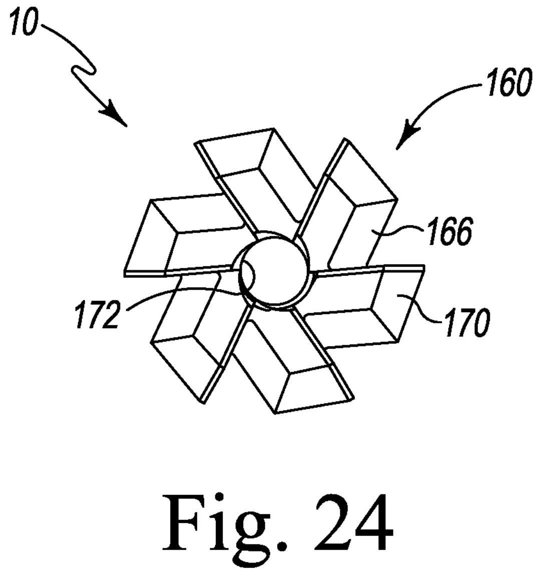
FIG. 24 is an end view of the cone reamer of FIG. 22.

The stem trial component 150 may also be used to guide a cone reamer 160 during a preliminary step in the orthopaedic surgical procedure to implant the cone augments 12, 112. As shown in FIGS. 22-24, the cone reamer 160 includes an elongated shaft 162 having a proximal end 164 that fits into the chuck of a rotary power tool or a manual handle (not shown). The cone reamer 160 also includes a cutting head 166 located at the opposite, distal end 168 of the shaft 162. The cutting head 166 of the cone reamer 160 includes a plurality of helical cutting flutes 170. The cutting head 166 is generally conical in shape. When the cone reamer 160 is positioned in the patient's tibia or femur and rotated, the cutting flutes 170 ream or otherwise cut the bone tissue to form a surgically-prepared cavity to accommodate the geometry of one of the broaches 14, 114. As such, the cone reamer 160 may be used to form an initial surgically-prepared cavity in the patient's bone, with one of the broaches 14, 114 then being used to form the final shape and size of the surgically-prepared cavity.

As shown in FIGS. 22 and 24, the cone reamer 160 has a threaded bore 172 formed in its distal end 168. Like the threaded bores 152 formed in the broaches 14, 114, the threaded bore 172 of the reamer 160 is sized to receive the threaded post 154 formed in the proximal end 156 of the stem trial component 150 so as to selectively secure the stem trial component 150 to the cone reamer 160. In such a way, and as discussed below in more detail, the stem trial component 150 may be used as a guide instrument during use of the cone reamer 160. Like the surgical broaches 14, 114, in the illustrative embodiment described herein, the cone reamer 160 is constructed with stainless steel. Other suitable materials may be used to fit the needs of a given design of the reamer 160.

As described above, the orthopaedic system 10 may be used to surgically-prepare a patient's knee to receive a revision knee prosthesis. In particular, as shown in FIGS. 25-31, the orthopaedic system 10 may be used to surgically prepare a patient's tibia 200 to receive a revision tibial prosthesis. As shown in FIGS. 32-36, the orthopaedic system 10 may also be used to surgically prepare a patient's femur 250 to receive a revision femoral prosthesis.

Figure 25:
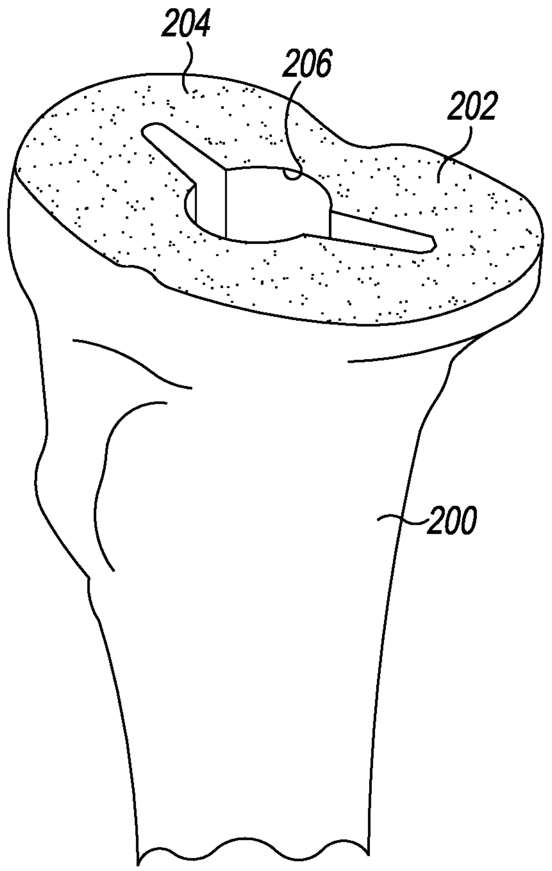
FIGS. 25-31 illustrate a number of steps of a surgical procedure to implant the tibial cone augment of FIGS. 1-4.

As shown in FIG. 25, the orthopaedic system 10 is used in a revision procedure in which a primary tibial implant has been removed from the proximal end 202 of the patient's tibia 200. As shown in FIG. 25, in a revision procedure, the proximal end 202 of the patient's tibia 200 includes a plurality of surfaces that had been previously surgically-shaped to receive the primary implant. During a revision procedure, the proximal end 202 of the patient's tibia 200 is further surgically-resected to prepare the bone to receive a revision tibial prosthesis. FIGS. 25-31 illustrate a number of exemplary steps of a procedure for surgically-preparing the proximal end 202 of the patient's tibia 200 during a revision procedure. It should be appreciated that any surgical procedure may include additional or fewer steps depending on the state of the patient's bony anatomy and the preferences of the surgeon.

Figure 26:
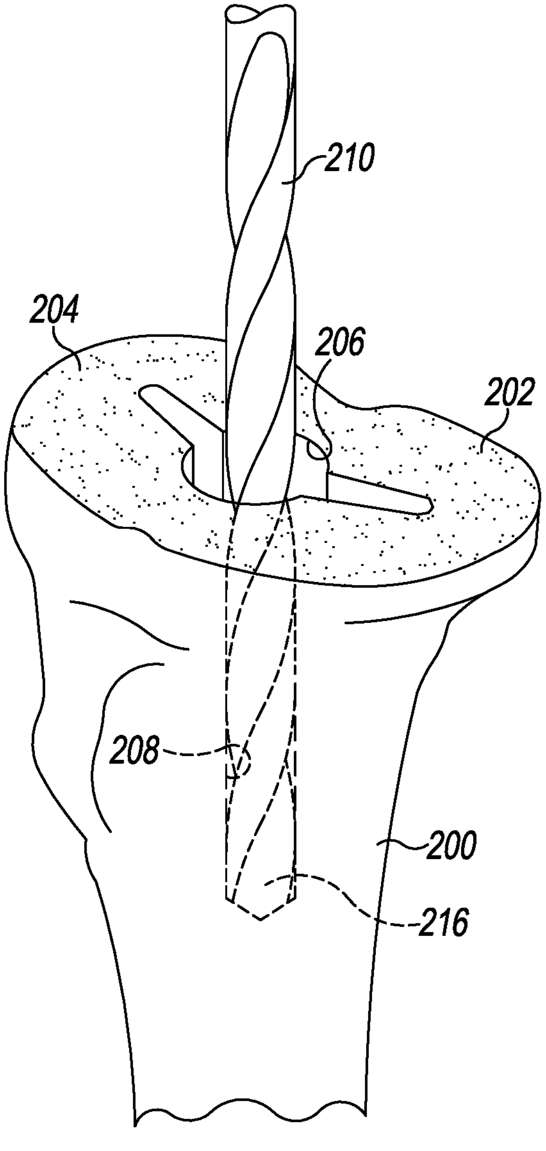

Referring specifically now to FIG. 25, the proximal end 202 of the patient's tibia 200 includes an opening 206 defined in a planar resected surfaces 204. The opening 206 was formed during the previous procedure to implant the primary implant and now permits the surgeon to access the intramedullary canal 208 of the patient's tibia subsequent to removal of the primary implant. With access to the intramedullary canal 208 now achieved, the surgeon then prepares the intramedullary canal 208 of the patient's tibia 200 to receive the stem of a revision tibial prosthesis. To do so, as shown in FIG. 26, the surgeon uses a canal reamer 210 to ream the portion of the patient's intramedullary canal 208 into which the stem component of the tibial revision prosthesis is implanted. To do so, the surgeon inserts the proximal end of the canal reamer 210 into the chuck of the manual handle or a rotary power tool. The surgeon then positions the cutting head 216 of the canal reamer 210 in the intramedullary canal 208 of the patient's tibia 200 and thereafter rotates the cutting head 216 manually (by use of a handle) or under the control of a rotary power tool. Such rotation of the cutting head 216 causes its cutting flutes 218 to ream or otherwise cut the bone tissue of the tibia 200. The canal reamer 210 is driven to a desired depth and then removed.

Figure 27:
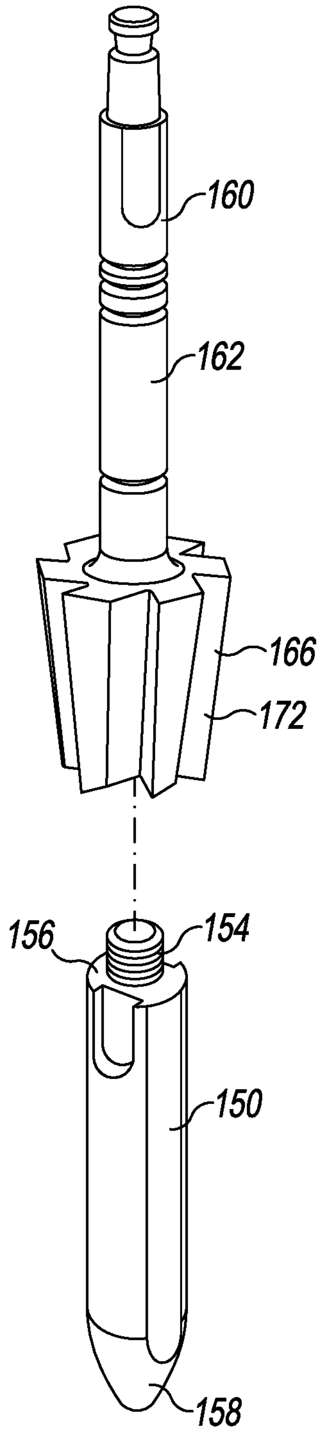
Figure 28:
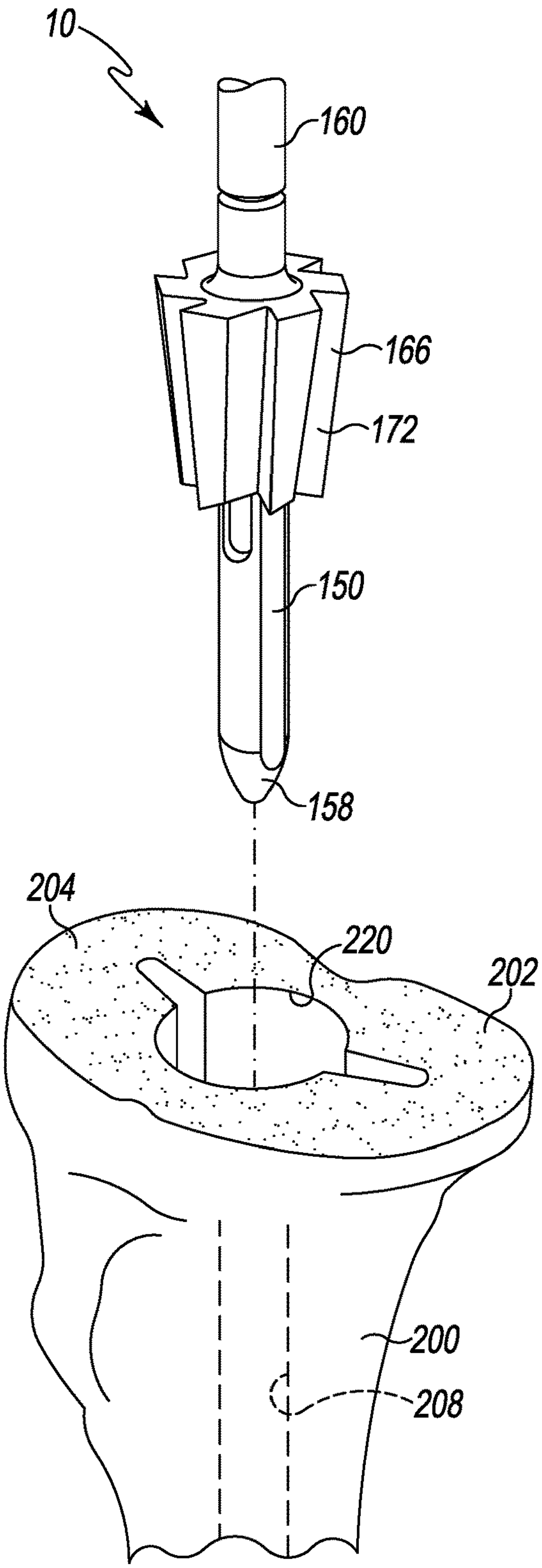

The surgeon then prepares the proximal end 202 of the patient's tibia 200 to receive one of the tibial cone augments 12. To do so, the surgeon first reams a starter cavity 220 in the proximal end 202 of the patient's tibia 200. As shown in FIGS. 27 and 28, the surgeon installs the stem trial component 150 on the cone reamer 160 by threading the stem's threaded post 154 into the threaded bore 172 formed in the distal end 168 of the reamer 160. It should be appreciated that the surgeon selects a stem trial component 150 that has a diameter that closely matches the diameter of the canal reamer 210 previously used to ream the patient's intramedullary canal 208 such that the stem trial component 150 forms a substantially tight fit within the reamed canal 208. In such a way, the stem trial component 150 is tightly captured within the reamed intramedullary canal 208 and, as a result, functions as a guide instrument for the cone reamer 160 so as to maintain the rotary axis of the reamer 160 in alignment with the center of the reamed intramedullary canal 208.

With the stem trial component 150 attached to the cone reamer 160, the surgeon inserts the proximal end of the cone reamer 160 into the chuck of the manual handle or a rotary power tool. The surgeon then advances the distal end 158 of the stem trial component 150 into the intramedullary canal 208 of the patient's tibia 200 and thereafter rotates the cutting head 166 (and hence the stem trial component 150 secured thereto) manually (by use of a handle) or under the control of a rotary power tool. Such rotation of the cutting head 166 causes its cutting flutes 170 to ream or otherwise cut the bone tissue of the proximal end 202 of the tibia 200 so as to form a reamed starter cavity 220 therein. The cone reamer 160 is driven to a desired depth—typically when the proximal end of the reamer's cutting head 166 is flush with the planar surface 204 of the proximal end 202 of the tibia 200—and is thereafter removed.

Figure 29:
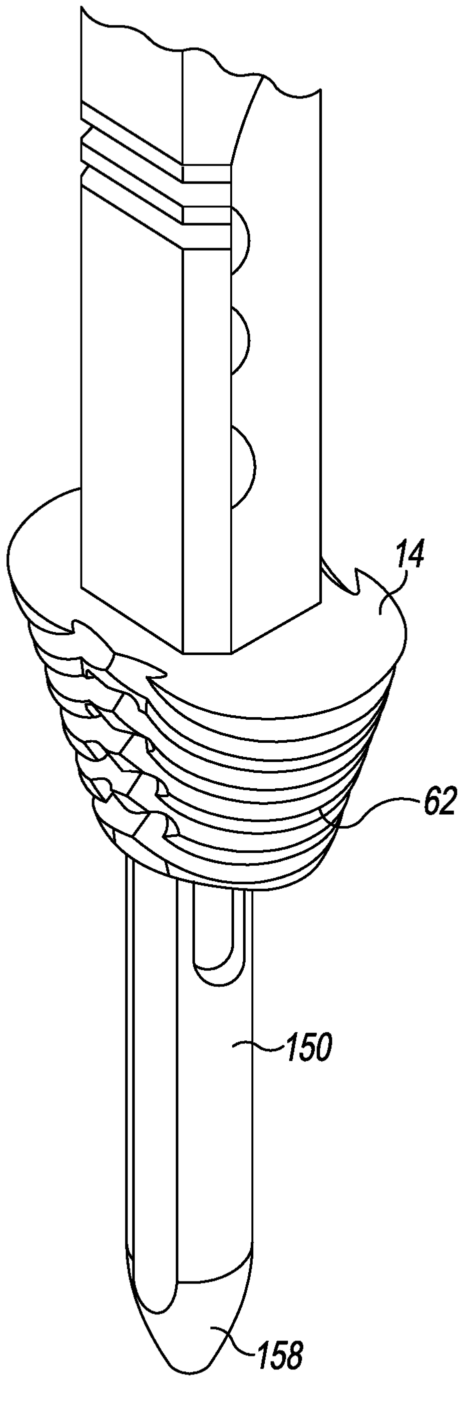
Figure 30:
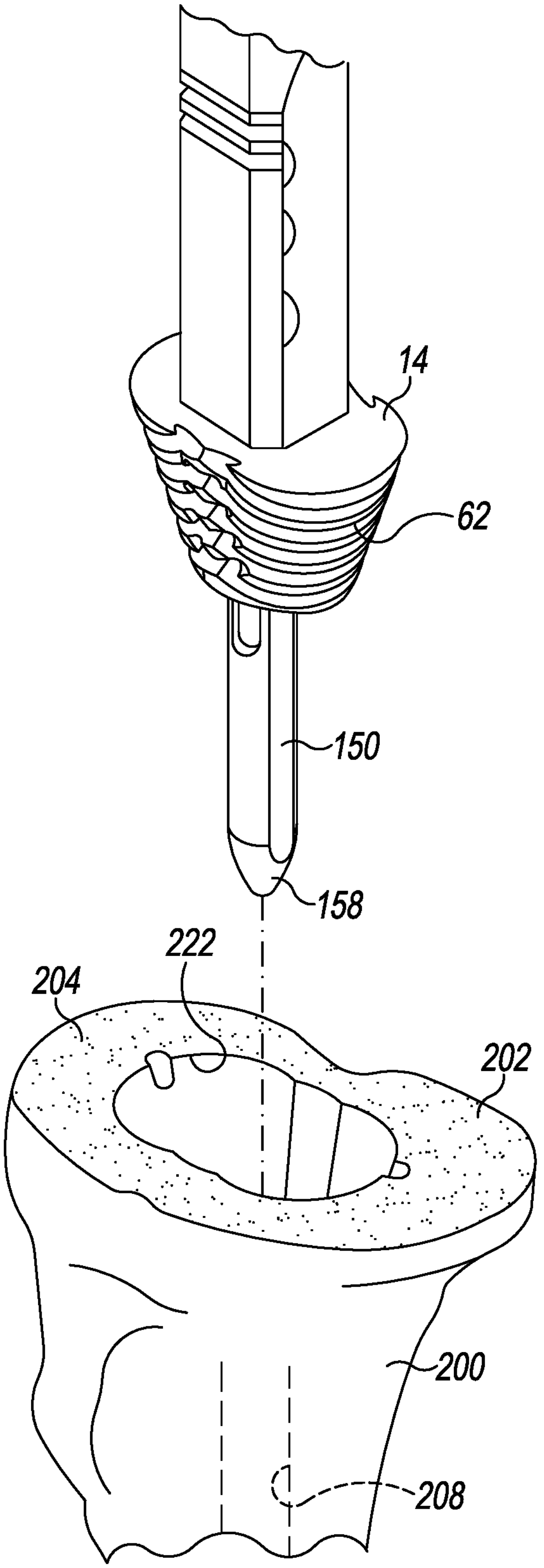

The surgeon then broaches a finished cavity 222 in the proximal end 202 of the patient's tibia 200. As shown in FIGS. 29 and 30, the surgeon installs the stem trial component 150 on the tibial surgical broach 14 by threading the stem's threaded post 154 into the threaded bore 152 formed in the distal end 154 of the tibial surgical broach 14. It should be appreciated that because the stem trial component 150 has a diameter that closely matches the diameter of the canal reamer 210, and thus is tightly captured within the reamed intramedullary canal 208, the stem trial component 150 functions a guide instrument for the tibial surgical broach 14 by maintaining the center of the broach's central lobe section 70 in alignment with the center of the reamed intramedullary canal 208.

With the stem trial component 150 attached to the tibial surgical broach 14, the surgeon then advances the distal end 158 of the stem trial component 150 into the intramedullary canal 208 of the patient's tibia 200. The surgeon continues to advance the broach 14 such that its cutting teeth 62 broach or otherwise cut the bone tissue of the proximal end 202 of the tibia 200 into a shape that corresponds to the shape of the tibial cone augment 12 so as to form the broached finished cavity 222 therein. Thereafter, the broach 14 and stem trial component 150 are removed.

Figure 31:
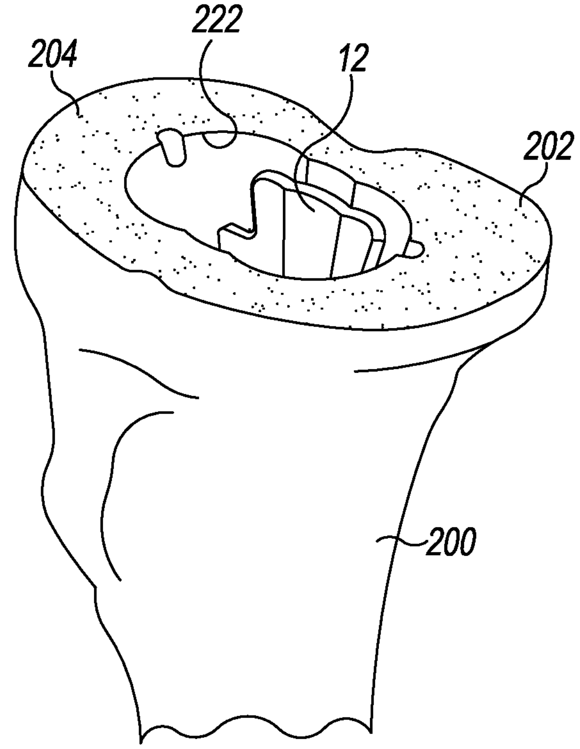

Once the finished cavity 222 has been broached, the tibial cone augment 12 is implanted, as shown in FIG. 31. As discussed above, if the surgeon determines that the patient's bone was over prepped (i.e., a larger finished cavity 222 was created than needed), the surgeon can simply substitute a larger tibial cone augment 12 than originally planned since the augments all "grow" along the same taper angles throughout the range of sizes. Similarly, in the case of when the surgeon determines that the patient's bone was under prepped (i.e., a smaller finished cavity 222 was created than needed), the surgeon can simply broach the cavity with the next size up broach 14. Alternatively, the surgeon can also substitute a smaller tibial cone augment 12 than originally planned and simply allow the smaller cone augment to sit a bit deeper in the prepared finished cavity 222 since the cavity 222 has been broached to common taper angles relative to the entire range of tibial cone augment sizes. Use of a smaller tibial cone augment 12 sitting deeper in the cavity 222 may be preferred over re-broaching the cavity to a larger size in the case of when the larger broach might be less than ideal due to the anatomy of the patient's tibia 200 or the magnitude of bone available in one direction or the other (e.g., the amount of bone available in the anterior/posterior direction may be limited even though ample bone exists for the larger broach in the medial/lateral direction).

Once the surgeon has implanted the desired size of the tibial cone augment 12, the surgeon may then implant a revision tibial prosthesis by installing its stem component through the tibial cone augment and thereafter cementing it in place within the bone.

Figure 32:
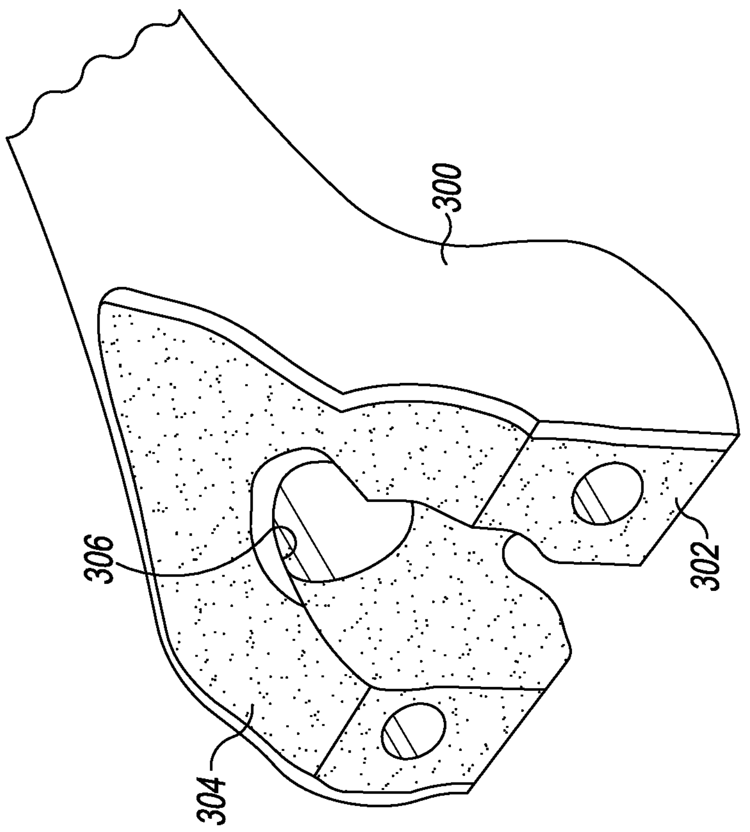
FIGS. 32-36 illustrate a number of steps of a surgical procedure to implant the femoral cone augment of FIGS. 12-14.

As illustrated in FIGS. 32-36, the orthopaedic system 10 may also be used to surgically prepare a patient's femur 300 to receive a revision femoral prosthesis. As shown in FIG. 32, the orthopaedic system 10 is used in a revision procedure in which a primary femoral implant has been removed from the distal end 302 of the patient's femur 300. In a femoral revision procedure, the distal end 302 of the patient's femur 300 includes a plurality of surfaces that had been previously surgically-shaped to receive the primary implant. During a revision procedure, the distal end 302 of the patient's femur 300 is further surgically-resected to prepare the bone to receive a revision femoral prosthesis. FIGS. 32-36 illustrate a number of exemplary steps of a procedure for surgically-preparing the distal end 302 of the patient's femur 300 during a revision procedure. It should be appreciated that any surgical procedure may include additional or fewer steps depending on the state of the patient's bony anatomy and the preferences of the surgeon.

Figure 33:
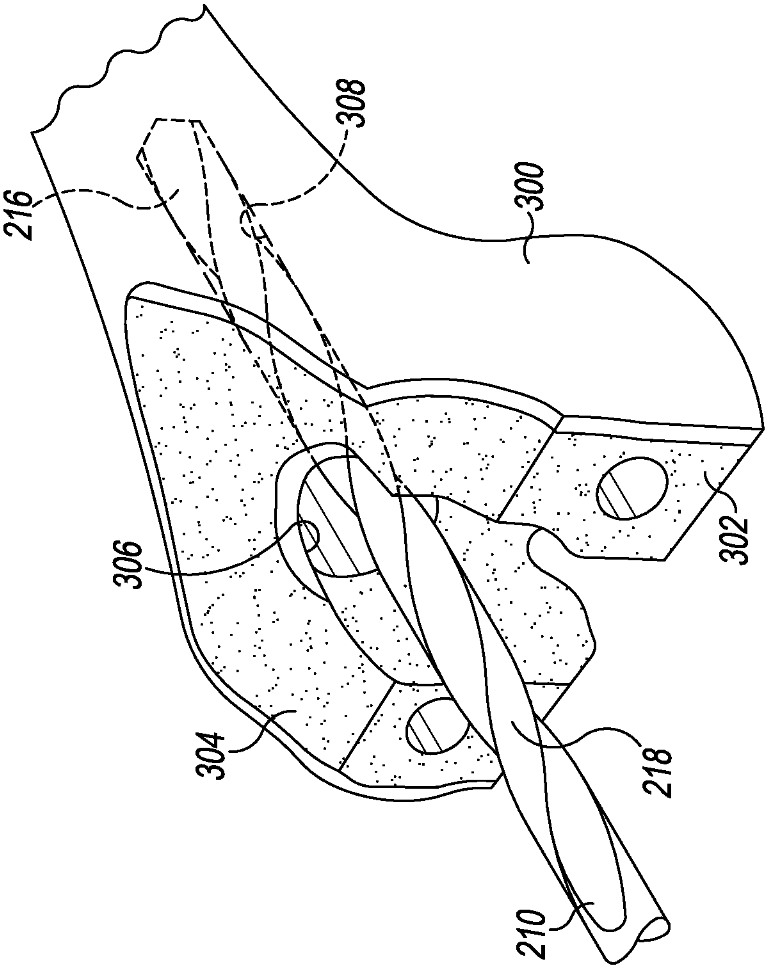

Referring now to FIG. 32, the distal end 302 of the patient's femur 300 includes an opening 306 defined in the resected surfaces 304. The opening 306 was formed during the previous procedure to implant the primary implant and now permits the surgeon to access the intramedullary canal 308 of the patient's femur subsequent to removal of the primary implant. With access to the intramedullary canal 308 achieved, the surgeon then prepares the intramedullary canal 308 of the patient's femur 300 to receive the stem of a revision femoral prosthesis. To do so, as shown in FIG. 33, the surgeon uses the canal reamer 210 to ream the portion of the patient's intramedullary canal 308 into which the stem component of the femoral revision prosthesis is implanted. It should be appreciated that the canal reamer 210 used by the surgeon to ream the femur 300 may, in practice, be embodied differently than the canal reamer 210 used to ream the patient's tibia 200. In any event, the surgeon inserts the proximal end of the canal reamer 210 into the chuck of the manual handle or a rotary power tool. The surgeon then positions the cutting head 216 of the canal reamer 210 in the intramedullary canal 308 of the patient's femur 300 and thereafter rotates the cutting head 216 manually (by use of a handle) or under the control of a rotary power tool. Such rotation of the cutting head 216 causes its cutting flutes 218 to ream or otherwise cut the bone tissue of the femur 300. The canal reamer 210 is driven to a desired depth and then removed.

Figure 34:
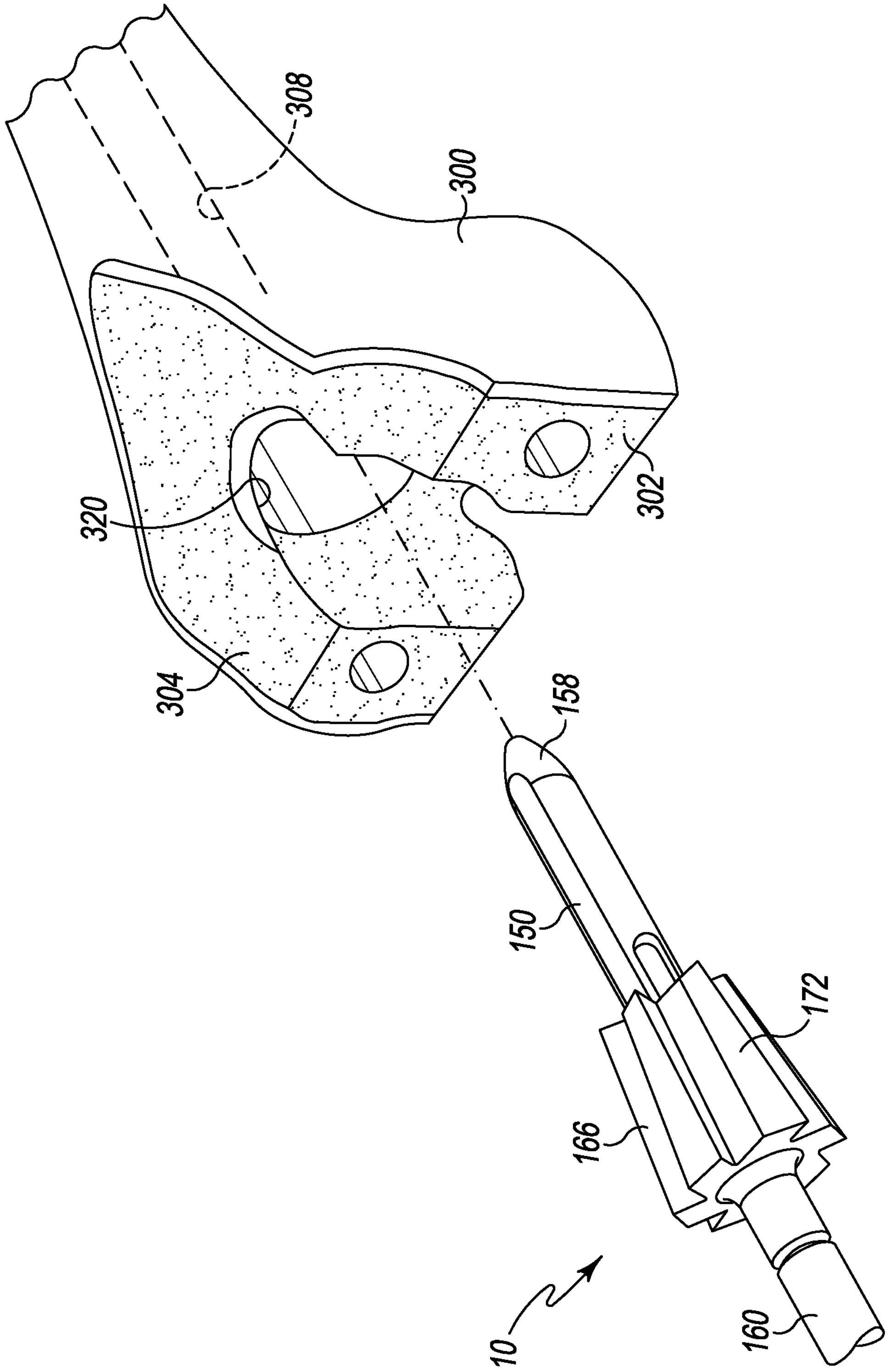

The surgeon then prepares the distal end 302 of the patient's femur 300 to receive one of the femoral cone augments 112. To do so, the surgeon first reams a starter cavity 320 in the distal end 302 of the patient's femur 300. As shown in FIG. 34, the surgeon installs the stem trial component 150 on the cone reamer 160 by threading the stem's threaded post 154 into the threaded bore 172 formed in the distal end 168 of the reamer 160. It should be appreciated that the surgeon selects a stem trial component 150 that has a diameter that closely matches the diameter of the canal reamer 210 previously used to ream the patient's intramedullary canal 308 such that the stem trial component 150 forms a substantially tight fit within the reamed canal 308. In such a way, the stem trial component 150 is tightly captured within the reamed intramedullary canal 308 and, as a result, functions as a guide instrument for the cone reamer 160 so as to maintain the rotary axis of the reamer 160 in alignment with the center of the reamed intramedullary canal 308.

With the stem trial component 150 attached to the cone reamer 160, the surgeon inserts the proximal end of the cone reamer 160 into the chuck of the manual handle or a rotary power tool. The surgeon then advances the distal end 158 of the stem trial component 150 into the intramedullary canal 308 of the patient's femur 300 and thereafter rotates the cutting head 166 (and hence the stem trial component 150 secured thereto) manually (by use of a handle) or under the control of a rotary power tool. Such rotation of the cutting head 166 causes its cutting flutes 170 to ream or otherwise cut the bone tissue of the distal end 302 of the femur 300 so as to form a reamed starter cavity 320 therein. The cone reamer 160 is driven to a desired depth and is thereafter removed.

Figure 35:
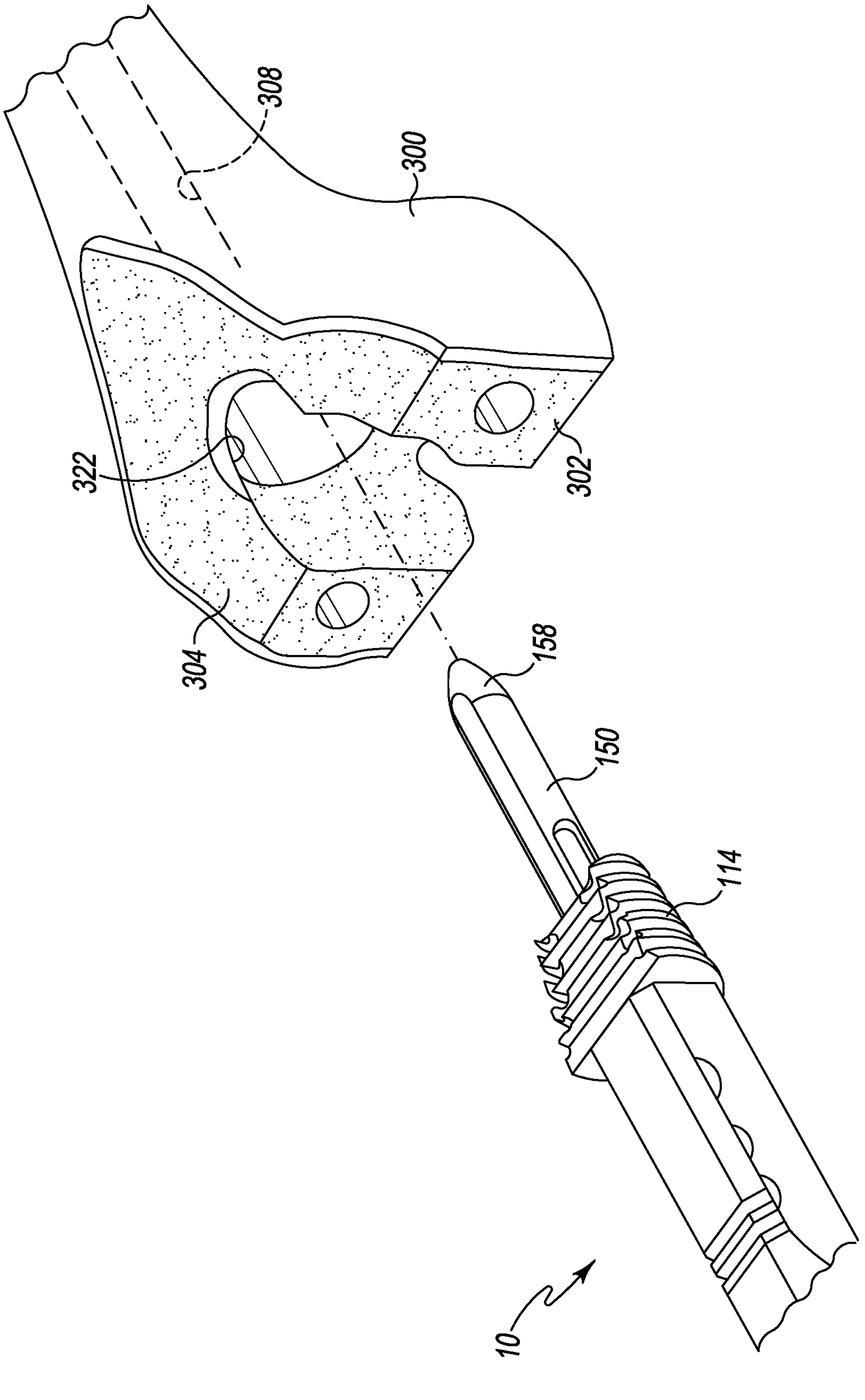

The surgeon then broaches a finished cavity 322 in the distal end 302 of the patient's femur 300. As shown in FIGS. 35, the surgeon installs the stem trial component 150 on the femoral surgical broach 114 by threading the stem's threaded post 154 into the threaded bore 152 formed in the distal end 154 of the femoral surgical broach 114. It should be appreciated that because the stem trial component 150 has a diameter that closely matches the diameter of the canal reamer 210, and thus is tightly captured within the reamed intramedullary canal 308, the stem trial component 150 functions a guide instrument for the femoral surgical broach 114 by maintaining the broach in a desired alignment relative to the center of the reamed intramedullary canal 308.

With the stem trial component 150 attached to the femoral surgical broach 114, the surgeon then advances the distal end 158 of the stem trial component 150 into the intramedullary canal 308 of the patient's femur 300. The surgeon continues to advance the broach 114 such that its cutting teeth 62 broach or otherwise cut the bone tissue of the distal end 302 of the femur 300 into a shape that corresponds to the shape of the femoral cone augment 112 thereby forming the broached finished cavity 322. Thereafter, the broach 114 and stem trial component 150 are removed.

Figure 36:
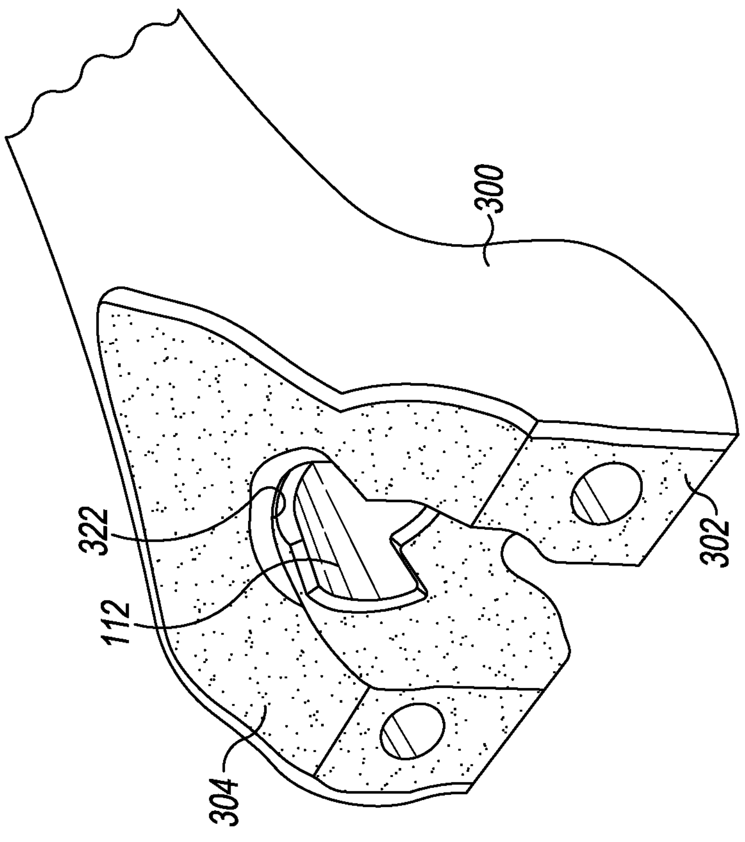

Once the finished cavity 322 has been broached, the femoral cone augment 112 is implanted, as shown in FIG. 36. As discussed above, if the surgeon determines that the patient's bone was over prepped (i.e., a larger finished cavity 322 was created than needed), the surgeon can simply substitute a larger femoral cone augment 112 than originally planned since the augments all "grow" along the same taper angles throughout the range of sizes. Similarly, in the case of when the surgeon determines that the patient's bone was under prepped (i.e., a smaller finished cavity 322 was created than needed), the surgeon can simply broach the cavity with the next size up broach 114. Alternatively, the surgeon can also substitute a smaller femoral cone augment 112 than originally planned and simply allow the smaller cone augment to sit a bit deeper in the prepared finished cavity 322 since the cavity 322 has been broached to common taper angles relative to the entire range of femoral cone augment sizes. Use of a smaller femoral cone augment 112 sitting deeper in the cavity 322 may be preferred over re-broaching the cavity to a larger size in the case of when the larger broach might be less than ideal due to the anatomy of the patient's femur 300 or the magnitude of bone available in one direction or the other (e.g., the amount of bone available in the anterior/posterior direction may be limited even though ample bone exists for the larger broach in the medial/lateral direction).

Once the surgeon has implanted the desired size of the femoral cone augment 112, the surgeon may then implant a revision femoral prosthesis by installing its stem component through the femoral cone augment and thereafter cementing it in place within the bone.

Referring now to FIGS. 37-41, there is shown another embodiment of a tibial cone augment. In particular, there is shown a modular tibial cone augment 400. Like the other tibial cone augments 12 described herein, the modular tibial cone augment 400 is configured to be implanted into a surgically-prepared cavity in the proximal end of the tibia of a patient so as to facilitate implantation of a revision tibial prosthesis.

The modular tibial cone augment 400 includes separate components which may be assembled to one another in various arrangements to create an implant of a desired configuration. In particular, the modular tibial cone augment 400 includes a central lobe component 402, a medial lobe component 404, and a lateral lobe component 406. In such a way, the modular tibial cone augment 400 may be assembled as a tri-lobe tibial augment (i.e., it has all three lobe components 402, 404, 406), a bi-lobe tibial augment (i.e., it has a central lobe component 402 and only one of the medial lobe component 404 or the lateral lobe component 406, but not both) or a concentric tibial augment (i.e., it has a central lobe component 402, but neither the medial lobe component 404 nor the lateral lobe component 406).

Figure 37:
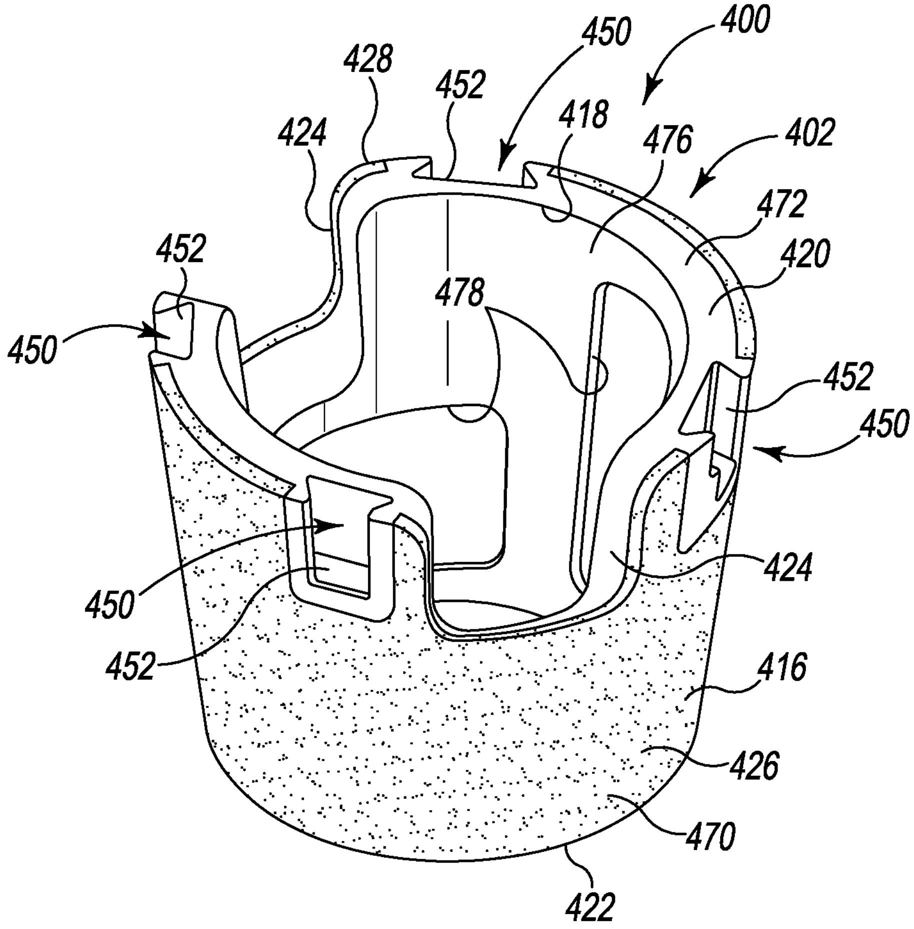
FIG. 37 is a perspective view of a central lobe component of a modular tibial cone augment.

As shown in FIG. 37, the central lobe component 402 includes a round, concentrically-shaped elongated hollow body 416 that is tapered downwardly from its superior end 420 to its inferior end 422. The central lobe component 402 also includes a bore 418 extending therethrough in the superior/inferior direction. The bore 418 is sized and shaped to receive a tibial stem component of a tibial revision prosthesis. As can be seen in FIG. 37, the body 416 of the central lobe component 402 has a cutout 424 formed on both its medial side 426 and its lateral side 428. The cutouts 424 allow for receipt of structures on the inferior side of a revision tibial tray such as one or more keels.

Figure 38:
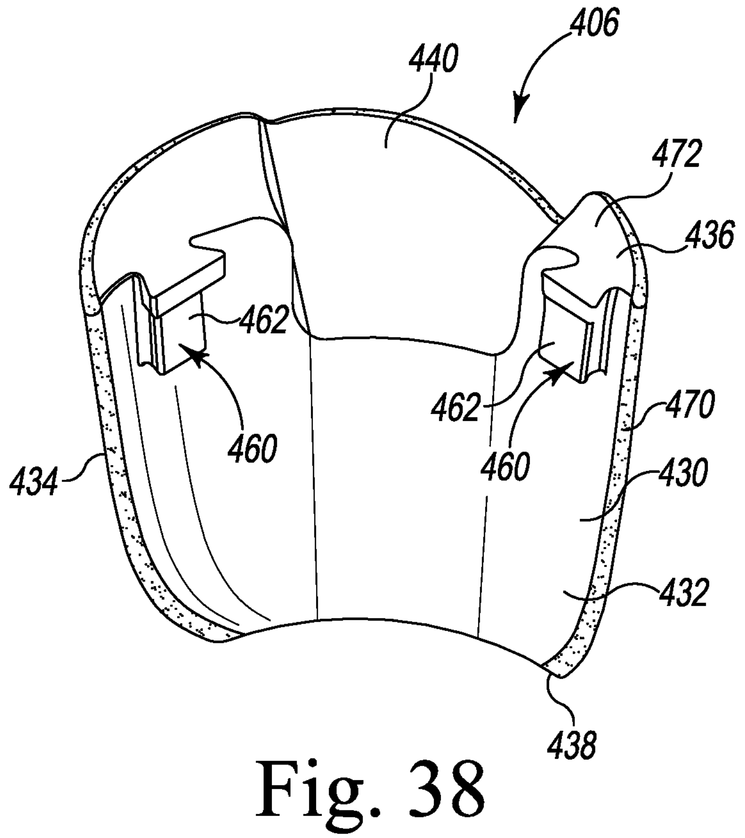
FIG. 38 is a perspective view of a lateral lobe component of a modular tibial cone augment.
Figure 39:
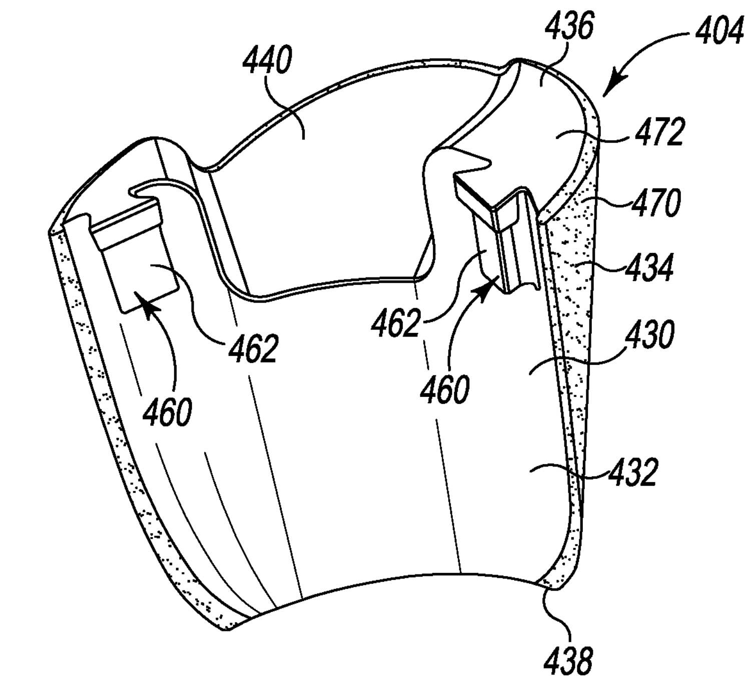
FIG. 39 is a perspective view of a medial lobe component of a modular tibial cone augment.
Figure 40:
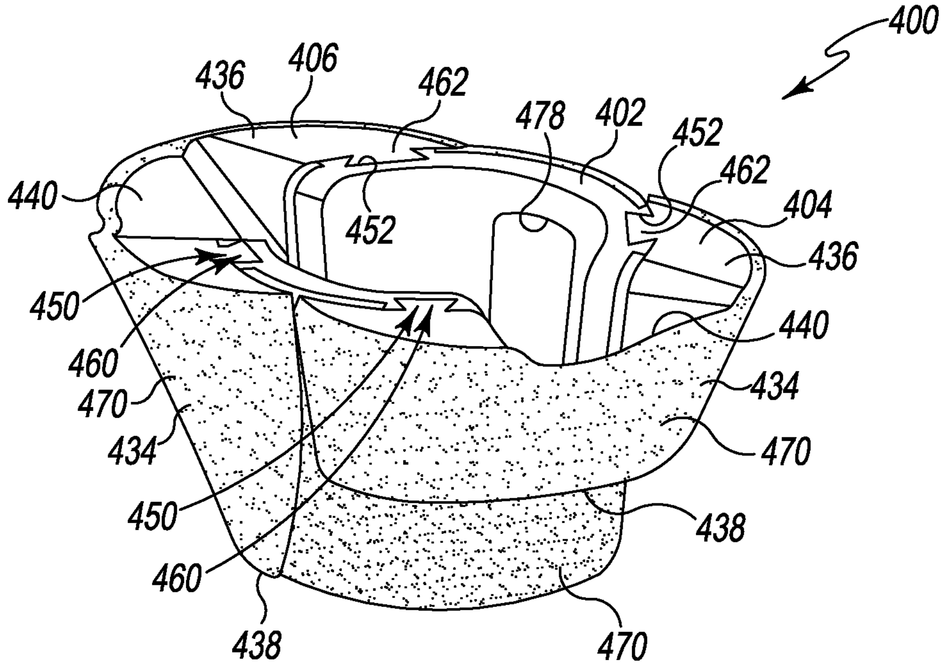
FIG. 40 is a perspective view showing the lobe components of FIGS. 37-39 assembled as a modular tri-lobe tibial cone augment.

As shown in FIGS. 38 and 39, both of the medial lobe component 404 and the lateral lobe component 406 have a body 430 that includes a curved inner sidewall 432 that corresponds in shape to the outer surface of the central lobe component 402. As such, when it is secured to the central lobe component 402, the inner sidewall 432 of the medial lobe component 404 corresponds in shape with the medial side 426 of the central lobe component's body 416. Similarly, when it is secured to the central lobe component 402, the inner sidewall 432 of the lateral lobe component 406 corresponds in shape with the lateral side 428 of the central lobe component's body 416. As can be seen in FIGS. 38-40, the medial lobe component 404 and the lateral lobe component 406 include a curved outer surface 434 that tapers downwardly from the component's superior end 436 to its inferior end 438. In such a way, the inferior end 438 of the side components 404, 406 blends into the outer surface of the central lobe component 402 when secured thereto.

Figure 41:
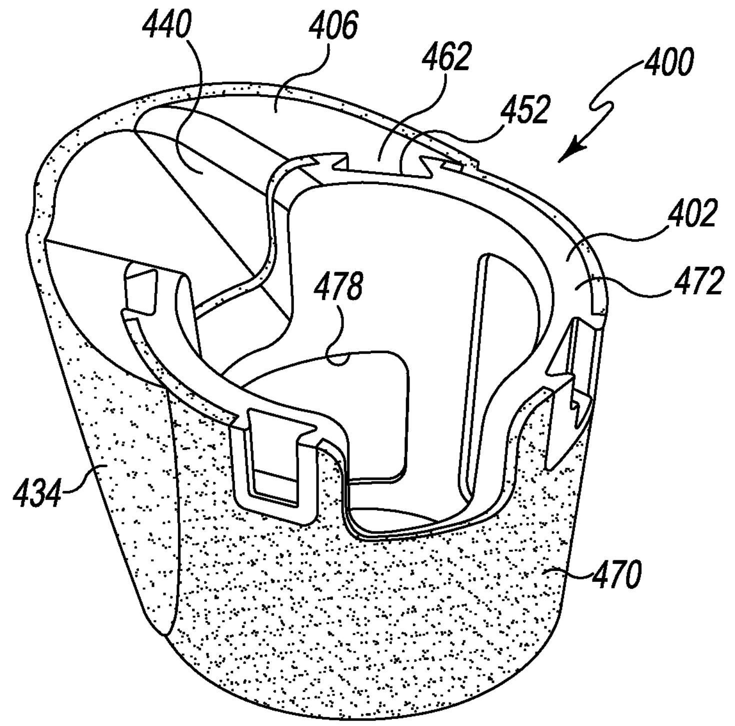
FIG. 41 is a perspective view showing the lobe components of FIGS. 37 and 38 assembled as a modular bi-lobe tibial cone augment

It should be appreciated that the side lobe components 404, 406 may be provided in a wide variety of geometries. In particular, the side lobe components 404, 406 may be provided in a wide range of widths, lengths, curvatures, etcetera to produce a wide range of options for a surgeon to customize the geometry of an assembled modular tibial cone augment 400. In such a way, the surgeon can use the modular tibial cone augment 400 to accommodate varying degrees of bone loss and/or varying patient anatomies The surface defining the superior end 436 of both the medial lobe component 404 and the lateral lobe component 406 has a recess 440 formed therein. As can be seen in FIGS. 40 and 41, the recesses 440 align with the cutouts 424 formed in the central lobe component 402 when either or both of the medial lobe component 404 and the lateral lobe component 406 are secured to the central lobe component 402. The recesses 440 cooperate with the cutouts 424 to allow for receipt of structures on the inferior side of a revision tibial tray such as one or more keels.

As can be seen in FIG. 37, the central lobe component 402 has a connector 450 formed on both its medial side 426 and its lateral side 428. The connectors 450 mate with connectors 460 formed in the medial lobe component 404 and the lateral lobe component 406 to allow one or both of the components 404, 406 to be secured to the central lobe component 402 during assembly of the modular tibial cone augment 400. In the illustrative embodiment described herein, the connectors 450, 460 define a dovetail joint. In such a way, the connectors 460 are embodied as a pair of dovetail-type tabs 462 that are received into a corresponding pair of dovetail-type slots 452 that embody the connectors 450 of the central lobe component 402. The tabs 462 and the slots 452 taper downwardly from their superior ends to their inferior ends. As such, a taper lock is created as the tabs 462 are advanced into the slots 452 thereby locking the components 404, 406 to the central lobe component 402. The radial distance between each of the pair of tabs 462 on the medial lobe component 404 is the same as the radial distance between each of the pair of tabs 462 on the lateral lobe component 406. As such, the side lobe components 404, 406 may, in practice, be installed on either side of the central lobe component 402. This enhances the flexibility of the modular tibial cone augment 400 since its side lobe components are interchangeable with one another and thus any of its side lobe components may be secured to either side of its central lobe component 402.

Like the body 16 of the tibial cone component 12 and the body 116 of the femoral cone augment 112 discussed above, the bodies 416, 430 of the lobe components 402, 404, 406 of the modular tibial cone augment 400 are illustratively embodied as a solid-metal base 472 having a porous-metal coating 470 disposed thereon. The solid-metal base 472 and the porous-metal coating 470 may be embodied and manufactured in a similar manner as the solid-metal base 32 and the porous metal coating 30 discussed above in regard to the tibial cone component 12, with all such features, methods, starting materials, and alternatives not being repeated herein for purposes of brevity. In the illustrative embodiment described herein, like as was described above in regard to the tibial cone augment 12, the porous-metal coating 470 is disposed on the solid-metal base 472 of the lobe components 402, 404, 406 by virtue of being additively manufactured contemporaneously with the solid-metal base 472 so as to create a common, monolithic component of the two metal structures.

As can be seen in FIGS. 37, 40, and 41, the inner sidewall 476 that defines the bore 418 of the hollow body 416 has a number of cement pockets 478 formed therein. Bone cement is received into the cement pockets 478 to increase adhesion of the cement to the modular tibial cone augment 400 during implantation of the tibial revision prosthesis.

In use, the modular tibial cone augment 400 may be used by a surgeon during a surgical procedure to implant a tibial revision prosthesis. During such a procedure, the surgeon will assess the patient's bone. Specifically, the surgeon will determine the condition of bone tissue of the proximal end of the patient's tibia. From there, the surgeon can determine the size and type of cone augment that is needed—e.g., a concentric, bi-lobe, or tri-lobe cone augment. The surgeon then forms a surgically-prepared cavity in the proximal end of the tibia of the tibia of the patient that corresponds to the size and type of tibial cone augment to be implanted.

The surgeon may then assemble a modular tibial cone augment 400 that corresponds to the shape of the surgically-prepared cavity by locking a selected medial lobe component 404 or a selected lateral lobe component 406—or both—to a selected central lobe component 402 so as to assemble a desired size and configuration of the tibial cone augment to be implanted. As discussed above, to fit the needs of a given surgical application, the modular tibial cone augment 400 may be assembled as a tri-lobe tibial augment (i.e., it has all three lobe components 402, 404, 406), a bi-lobe tibial augment (i.e., it has a central lobe component 402 and only one of the medial lobe component 404 or the lateral lobe component 406, but not both) or a concentric tibial augment (i.e., it has a central lobe component 402, but neither the medial lobe component 404 nor the lateral lobe component 406). Moreover, each of the components 402, 404, 406 may be provided in a range of shapes and sizes to increase the surgeon's options.

Once the desired arrangement of the modular tibial cone augment 400 has been assembled, the surgeon may then install the assembled construct in the surgically-prepared cavity formed in the proximal end of the tibia.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic system, comprising:

a plurality of tibial cone augments configured to be implanted into a surgically-prepared cavity in a proximal end of a tibia of a patient, wherein each of the plurality of tibial cone augments has (i) a medial/lateral augment taper angle defined by an angle formed by an entirety of its medial-most edge and an entirety of its lateral-most edge from an inferior-most end of each edge to a superior-most end of each edge, and (ii) a medial/lateral augment width defined by its width at its widest medial/lateral dimension, wherein the medial/lateral augment taper angle of each of the plurality of tibial cone augments is the same as each of the other of the plurality of tibial cone augments, and the medial/lateral augment width of each of the plurality of tibial cone augments is different from each of the other of the plurality of tibial cone augments, and a plurality of tibial surgical broaches having cutting teeth configured to cut bone to form the surgically-prepared cavity in the proximal end of the tibia of the patient, wherein each of the plurality of tibial surgical broaches has (i) a medial/lateral broach taper angle defined by an angle formed by an entirety of an imaginary line extending along and connecting medial-most edges of each of the cutting teeth and an entirety of an imaginary line extending along and connecting lateral-most edges of each of the cutting teeth from a distal-most end of each imaginary line to a proximal-most end of each imaginary line, and (ii) a medial/lateral broach width defined by its width at its widest medial/lateral dimension, wherein the medial/lateral broach taper angle of each of the plurality of tibial surgical broaches is the same as each of the other of the plurality of tibial surgical broaches, the medial/lateral broach taper angle is the same as the medial/lateral augment taper angle, and the medial/lateral broach width of each of the plurality of tibial surgical broaches is different from each of the other of the plurality of tibial surgical broaches.

2. The orthopaedic system of claim 1, wherein:

each of the plurality of tibial cone augments has an anterior/posterior augment taper angle defined by an angle formed by an entirety of its anterior-most edge and an entirety of its posterior-most edge from an inferior-most end of each edge to a superior-most end of each edge, wherein the anterior/posterior augment taper angle of each of the plurality of tibial cone augments is the same as each of the other of the plurality of tibial cone augments, and each of the plurality of tibial surgical broaches has an anterior/posterior broach taper angle defined by an angle formed by an entirety of an imaginary line extending along and connecting anterior-most edges of each of the cutting teeth and an entirety of an imaginary line extending along and connecting posterior-most edges of each of the cutting teeth from a distal-most end of each imaginary line to a proximal-most end of each imaginary line, wherein (i) the anterior/posterior broach taper angle of each of the plurality of tibial surgical broaches is the same as each of the other of the plurality of tibial surgical broaches, and (ii) the anterior/posterior broach taper angle is the same as the anterior/posterior augment taper angle.

3. The orthopaedic system of claim 1, wherein each of the plurality of tibial cone augments comprises a tri-lobe tibial cone augment.

4. The orthopaedic system of claim 1, wherein each of the plurality of tibial cone augments comprises a bi-lobe tibial cone augment.

5. The orthopaedic system of claim 1, further comprising a stem trial component having a threaded post extending from a proximal end thereof, wherein:

each of the plurality of tibial surgical broaches has a threaded aperture formed in a distal end thereof, and the threaded aperture formed in each of the plurality of tibial surgical broaches is sized to threadingly receive the threaded post of the stem trial component.

6. An orthopaedic system, comprising:

a plurality of femoral cone augments configured to be implanted into a surgically-prepared cavity in a distal end of a femur of a patient, wherein each of the plurality of femoral cone augments has (i) a medial/lateral augment taper angle defined by an angle formed by an entirety of its medial-most edge and an entirety of its lateral-most edge from an inferior-most end of each edge to a superior-most end of each edge, and (ii) a medial/lateral augment width defined by its width at its widest medial/lateral dimension, wherein the medial/lateral augment taper angle of each of the plurality of femoral cone augments is the same as each of the other of the plurality of femoral cone augments, and the medial/lateral augment width of each of the plurality of femoral cone augments is different from each of the other of the plurality of femoral cone augments, and a plurality of femoral surgical broaches having cutting teeth configured to cut bone to form the surgically-prepared cavity in the distal end of the femur of the patient, wherein each of the plurality of femoral surgical broaches has (i) a medial/lateral broach taper angle defined by an angle formed by an entirety of an imaginary line extending along and connecting medial-most edges of each of the cutting teeth and an entirety of an imaginary line extending along and connecting lateral-most edges of each of the cutting teeth from a distal-most end of each imaginary line to a proximal-most end of each imaginary line, and (ii) a medial/lateral broach width defined by its width at its widest medial/lateral dimension, wherein the medial/lateral broach taper angle that of each of the plurality of femoral surgical broaches is the same as each of the other of the plurality of femoral surgical broaches, the medial/lateral broach taper angle is the same as the medial/lateral augment taper angle, and the medial/lateral broach width that of each of the plurality of femoral surgical broaches is different from each of the other of the plurality of femoral surgical broaches.

7. The orthopaedic system of claim 6, wherein:

each of the plurality of femoral cone augments has an anterior/posterior augment taper angle defined by an angle formed by an entirety of its anterior-most edge and an entirety of its posterior-most edge from an inferior-most end of each edge to a superior-most end of each edge, wherein the anterior/posterior augment taper angle of each of the plurality of femoral cone augments is the same as each of the other of the plurality of femoral cone augments, and each of the plurality of femoral surgical broaches has an anterior/posterior broach taper angle defined by an angle formed by an entirety of an imaginary line extending along and connecting anterior-most edges of each of the cutting teeth and an entirety of an imaginary line extending along and connecting posterior-most edges of each of the cutting teeth from a distal-most end of each imaginary line to a proximal-most end of each imaginary line, wherein (i) the anterior/posterior broach taper angle of each of the plurality of femoral surgical broaches is the same as each of the other of the plurality of femoral surgical broaches, and (ii) the anterior/posterior broach taper angle is the same as the anterior/posterior augment taper angle.

8. The orthopaedic system of claim 6, further comprising a stem trial component having a threaded post extending from a proximal end thereof, wherein:

each of the plurality of femoral surgical broaches has a threaded aperture formed in a distal end thereof, and the threaded aperture formed in each of the plurality of femoral surgical broaches is sized to threadingly receive the threaded post of the stem trial component.

9. The orthopaedic system of claim 6, wherein the imaginary line extending along and connecting the medial-most edges of each of the cutting teeth and the imaginary line extending along and connecting the lateral-most edges of each of the cutting teeth are each straight lines.

10. An orthopaedic system, comprising:

a plurality of knee cone augments configured to be implanted into a surgically-prepared cavity in an end of a bone of a patient's knee, wherein each of the plurality of knee cone augments has (i) a medial/lateral augment taper angle defined by an angle formed by an entirety of its medial-most edge and an entirety of its lateral-most edge from an inferior-most end of each edge to a superior-most end of each edge, and (ii) a medial/lateral augment width defined by its width at its widest medial/lateral dimension, wherein the medial/lateral augment taper angle of each of the plurality of knee cone augments is the same as each of the other of the plurality of knee cone augments, and the medial/lateral augment width of each of the plurality of knee cone augments is different from each of the other of the plurality of knee cone augments, and a plurality of knee surgical broaches having cutting teeth configured to cut bone to form the surgically-prepared cavity in the end of the bone of the patient's knee, wherein each of the plurality of knee surgical broaches has (i) a medial/lateral broach taper angle defined by an angle formed by an entirety of an imaginary line extending along and connecting medial-most edges of each of the cutting teeth and an entirety of an imaginary line extending along and connecting lateral-most edges of each of the cutting teeth from a distal-most end of each imaginary line to a proximal-most end of each imaginary line, and (ii) a medial/lateral broach width defined by its width at its widest medial/lateral dimension, wherein the medial/lateral broach taper angle of each of the plurality of knee surgical broaches is the same as each of the other of the plurality of knee surgical broaches, the medial/lateral broach taper angle is the same as the medial/lateral augment taper angle, and the medial/lateral broach width that of each of the plurality of knee surgical broaches is different from each of the other of the plurality of knee surgical broaches.

11. The orthopaedic system of claim 10, wherein:

each of the plurality of knee cone augments has an anterior/posterior augment taper angle defined by an angle formed by an entirety of its anterior-most edge and an entirety of its posterior-most edge from an inferior-most end of each edge to a superior-most end of each edge, wherein the anterior/posterior augment taper angle of each of the plurality of knee cone augments is the same as each of the other of the plurality of knee cone augments, and each of the plurality of knee surgical broaches has an anterior/posterior broach taper angle defined by an angle formed by an entirety of an imaginary line extending along and connecting anterior-most edges of each of the cutting teeth and an entirety of an imaginary line extending along and connecting posterior-most edges of each of the cutting teeth from a distal-most end of each imaginary line to a proximal-most end of each imaginary line, wherein the anterior/posterior broach taper angle of each of the plurality of knee surgical broaches is the same as each of the other of the plurality of knee surgical broaches, the anterior/posterior broach taper angle is the same as the anterior/posterior augment taper angle.

12. The orthopaedic system of claim 10, wherein each of the plurality of knee cone augments comprises a tri-lobe tibial cone augment.

13. The orthopaedic system of claim 10, wherein each of the plurality of knee cone augments comprises a bi-lobe tibial cone augment.

14. The orthopaedic system of claim 10, wherein each of the plurality of knee cone augments comprises a femoral cone augment.

15. The orthopaedic system of claim 10, further comprising a stem trial component having a threaded post extending from a proximal end thereof, wherein:

each of the plurality of knee surgical broaches has a threaded aperture formed in a distal end thereof, and the threaded aperture formed in each of the plurality of knee surgical broaches is sized to threadingly receive the threaded post of the stem trial component.

* * * * *